US010435536B2

(12) United States Patent
Swanzy

(10) Patent No.: US 10,435,536 B2
(45) Date of Patent: Oct. 8, 2019

(54) ZINC OXIDE COMPLEXES

(71) Applicant: Mary Kay Inc., Addison, TX (US)

(72) Inventor: James Swanzy, Arlington, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 16/026,951

(22) Filed: Jul. 3, 2018

(65) Prior Publication Data
US 2019/0040228 A1 Feb. 7, 2019

Related U.S. Application Data

(60) Continuation of application No. 15/499,478, filed on Apr. 27, 2017, now Pat. No. 10,053,550, which is a division of application No. 15/004,153, filed on Jan. 22, 2016, now Pat. No. 9,657,036, which is a continuation of application No. 14/560,979, filed on Dec. 4, 2014, now Pat. No. 9,273,071, which is a continuation of application No. 13/770,317, filed on Feb. 19, 2013, now Pat. No. 8,933,257, which is a continuation of application No. 13/285,807, filed on Oct. 31, 2011, now Pat. No. 8,404,743.

(60) Provisional application No. 61/408,307, filed on Oct. 29, 2010.

(51) Int. Cl.
A61K 8/58 (2006.01)
C08K 5/00 (2006.01)
A61Q 19/08 (2006.01)
A61K 8/35 (2006.01)
A61K 8/27 (2006.01)
A61Q 19/02 (2006.01)
C07F 3/00 (2006.01)
A61Q 19/00 (2006.01)
C07F 3/06 (2006.01)
A61Q 19/04 (2006.01)
A61Q 17/04 (2006.01)
A61Q 5/12 (2006.01)
A61Q 5/02 (2006.01)
A61Q 3/00 (2006.01)
A61Q 1/02 (2006.01)

(52) U.S. Cl.
CPC .............. C08K 5/0091 (2013.01); A61K 8/27 (2013.01); A61K 8/35 (2013.01); A61K 8/58 (2013.01); A61Q 19/00 (2013.01); A61Q 19/007 (2013.01); A61Q 19/02 (2013.01); A61Q 19/08 (2013.01); C07F 3/003 (2013.01); C07F 3/06 (2013.01); A61K 2800/10 (2013.01); A61K 2800/58 (2013.01); A61Q 1/02 (2013.01); A61Q 3/00 (2013.01); A61Q 5/02 (2013.01); A61Q 5/12 (2013.01); A61Q 17/04 (2013.01); A61Q 19/04 (2013.01); C07B 2200/13 (2013.01)

(58) Field of Classification Search
CPC ............................... C08K 5/0091; A61K 8/58
See application file for complete search history.

(56) References Cited

U.S. PATENT DOCUMENTS

| 2,445,724 | A | 7/1948 | Smith |
| 4,316,852 | A | 2/1982 | Blachford |
| 4,837,010 | A | 6/1989 | Hotta et al. |
| 6,558,710 | B1 | 5/2003 | Godfrey |
| 6,689,894 | B1 | 2/2004 | Chen |
| 7,244,416 | B2 | 7/2007 | Meyer et al. |
| 7,547,454 | B2 | 6/2009 | Gupta |
| 7,550,504 | B2 | 6/2009 | Pablos |
| 8,404,743 | B2 | 3/2013 | Swanzy |
| 8,933,257 | B2 | 1/2015 | Swanzy |
| 9,273,071 | B2 | 3/2016 | Swanzy |
| 9,657,036 | B2 | 5/2017 | Swanzy |
| 10,053,550 | B2 * | 8/2018 | Swanzy .................. C07F 3/003 |
| 2009/0155194 | A1 | 6/2009 | Meyer et al. |

FOREIGN PATENT DOCUMENTS

JP 2004-161652 6/2004

OTHER PUBLICATIONS

"Ascorbic acid." *Wikipedia. The Free Encyclopedia.* Wikipedia Foundation, Inc. Jan. 25, 2012. Web. Jan. 28, 2012. <http://en.wikipedia.org/wiki/Ascorbic_acid>.
"Avobenzone." *Wikipedia, The Free Encyclopedia.* Wikipedia Foundation, Inc. Feb. 21, 2010. Web. Mar. 26, 2010. <http://en.wikipedia.org/wiki/Avobenzone>.
"Azelaic acid." *Wikipedia, The Free Encyclopedia.* Wikipedia Foundation, Inc. Mar. 8, 2010. Web. Mar. 31, 2010. <http://en.wikipedia.org/wiki/Azelaic_acid>.
"Citric acid." *Wikipedia, The Free Encyclopedia.* Wikipedia Foundation, Inc. Mar. 31, 2010. Web. Mar. 31, 2010. <http://en.wikipedia.orglwiki/Citric_acid>.
"Glycolic acid." *Wikipedia, The Free Encyclopedia.* Wikipedia Foundation, Inc. Feb. 24, 2010. Web. Mar. 31, 2010. <http://en.wikipedia.org/wiki/Azelaic_acid>.
"Hydroxproline." *Wikipedia, The Free Encyclopedia.* Wikipedia Foundation, Inc. Feb. 12, 2010. Web. Mar. 31, 2010. <http://en.wikipedia.org/wiki/hydroxproline>.
"Kojic acid." *Wikipedia, The Free Encyclopedia.* Wikipedia Foundation, Inc. Mar. 21, 2010. Web. Mar. 31, 2010. <http://en.wikipedia.org/wiki/kojic_acid>.
"Lactic acid." *Wikipedia, The Free Encyclopedia.* Wikipedia Foundation, Inc. Mar. 25, 2010. Web. Mar. 31, 2010. <http://en.wikipedia.org/wiki/Lactic_acid>.

(Continued)

Primary Examiner — Golam M Shameem
(74) Attorney, Agent, or Firm — Norton Rose Fulbright US LLP

(57) ABSTRACT

A method of vulcanizing rubber is disclosed. The method can include adding to un-vulcanized rubber a complex comprising mercaptobenzothiazole chemically bound to zinc oxide, and vulcanizing the rubber.

10 Claims, 14 Drawing Sheets

(56) References Cited

OTHER PUBLICATIONS

"Malic acid." *Wikipedia, The Free Encyclopedia.* Wikipedia Foundation, Inc. Feb. 4, 2010. Web. Mar. 31, 2010. <http://en.wikipedia.org/wiki/Malic_acid>.
"Oleic acid." *Wikipedia, The Free Encyclopedia.* Wikipedia Foundation, Inc. Mar. 12, 2010. Web. Mar. 31, 2010. <http://en.wikipedia.org/wiki/Oleic_acid>.
"Phenol." *Wikipedia, The Free Encyclopedia.* Wikipedia Foundation, Inc. Mar. 31, 2010. Web. Mar. 31, 2010. <http://en.wikipedia.org/wiki/Phenol>.
"Physical Properties of Zinc Oxide—CAS 1314-13-2," International Zinc Association. Available online at http://www.znoxide.org/properties.html Accessed Oct. 4, 2012.
"Salicylic acid." *Wikipedia, The Free Encyclopedia.* Wikipedia Foundation, Inc. Mar. 24, 2010. Web. Mar. 31, 2010. <http:/ /en.wikipedia.org/wiki/Salicylic_acid>.
"UKPID Monograph: Zinc Oxide" National Poisons Information Service Center, United Kingdom. IPCS INCHEM Home. Available online at http://www.inchem.org/documents/ukpids/ukpids/ukpid87.htm. Accessed Oct. 4, 2010.
"Zinc oxide." *Wikipedia, The Free Encyclopedia.* Wikipedia Foundation, Inc. Mar. 20, 2010. Web. Mar. 26, 2010. <http://en.wikipedia.org/wikilzinc_oxide>.
"Zinc oxide." *Wikipedia, The Free Encyclopedia.* Wikipedia Foundation, Inc. Oct. 4, 2010. Web. Oct. 4, 2010. <http://en.wikipedia.org/wikilzinc_oxide>.
Depew, "Reactions during vulcanization," *Ind. Eng. Chem.,* 24(5):565-568, 1932.
International Search Report and Written Opinion, issued in International Patent Application No. PCT/US2011/058605, dated May 16, 2012.
Merinville et al., "Exfoliation for sensitive skin with neutralized salicylic acid?" *IFSCC Magazine,* 11(2): 115-119, 2008.
Nocil Limited—Arvind Mafatlal Group "Vulcanization & Accelerators" Date: Unknown, pp. 1-35.
Osman et al., "Monoglycerides: I. Synthesis by direct esterification of fatty acids and glycerol," *Fette, Seifen, Anstrichmittel,* 70(5):331-333, 1968.
Ross and Aniko, "Surface reactions of ethyl stearate and stearic acid with zinc, manganese and their oxides," *Surface Technology,* 21(4):361-377, 1984.
Vander Kool, James "Changing Elastomer Properties with Zinc Soaps" *RubberNews.com* May 23, 1994. Retrieved on Apr. 17, 2018 from http://www.rubbernews.com/article/19940523/ISSUE/305239961?template=printart.

* cited by examiner

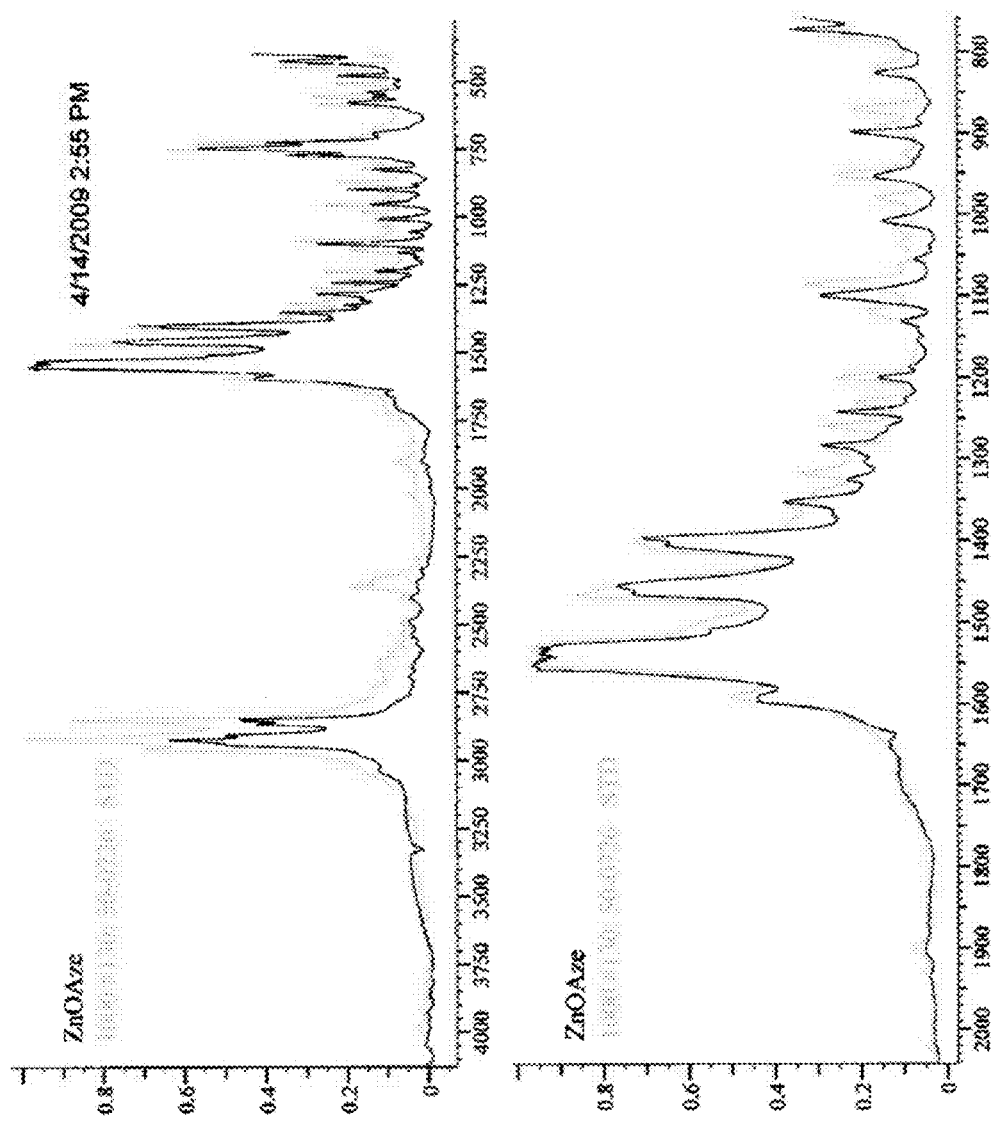
FIGS. 2B-C

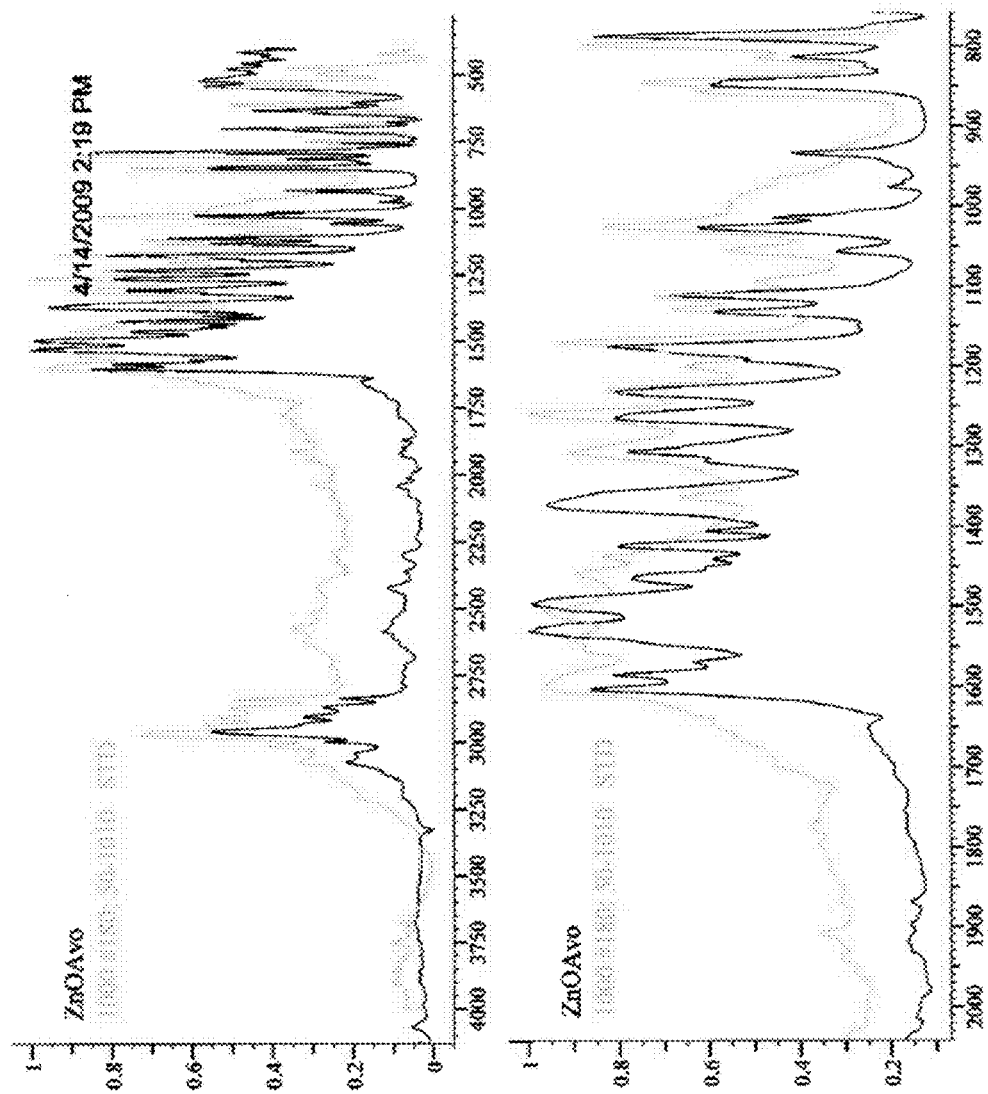
FIGS. 3B-C

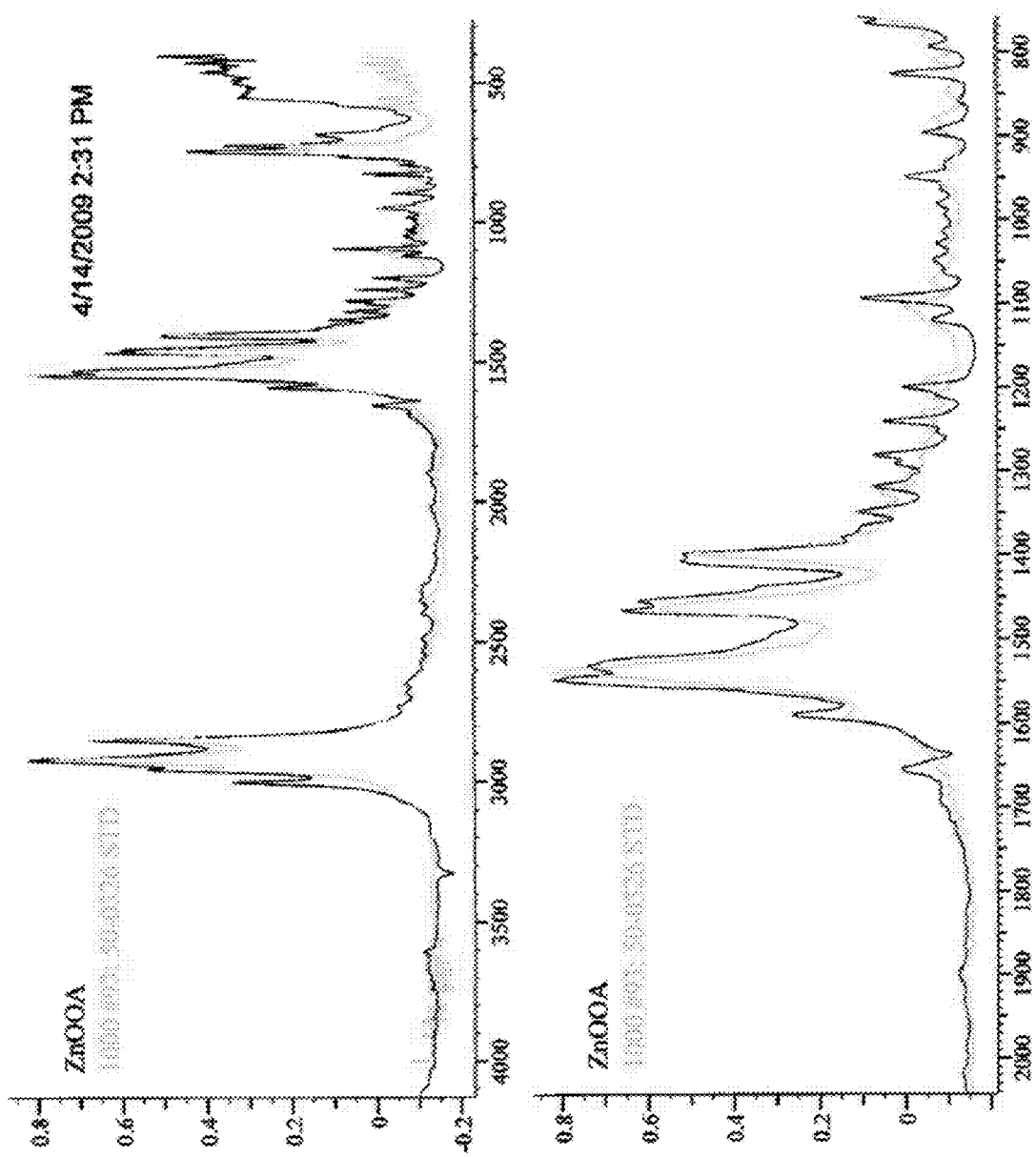
FIGS. 4B-C

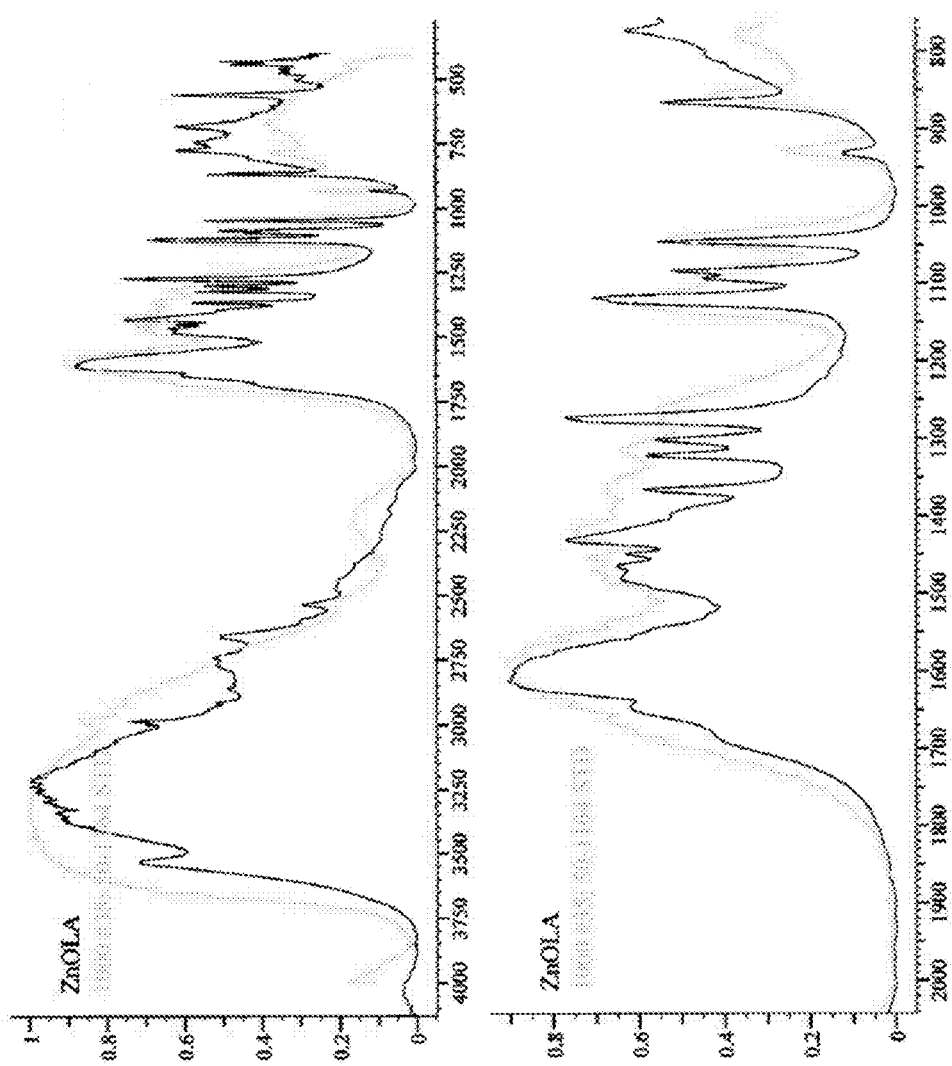
FIGS. 6B-C

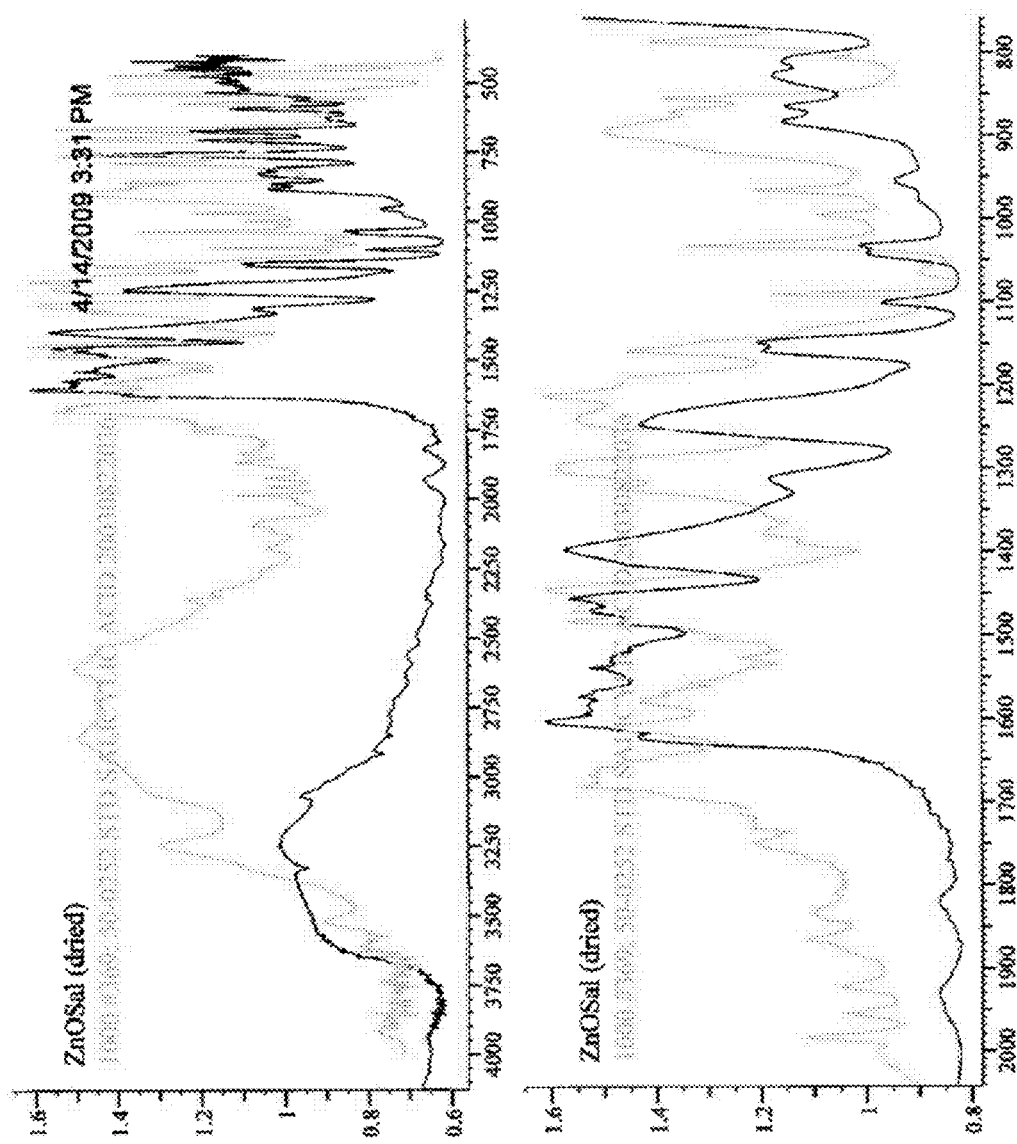
FIGS. 7B-C

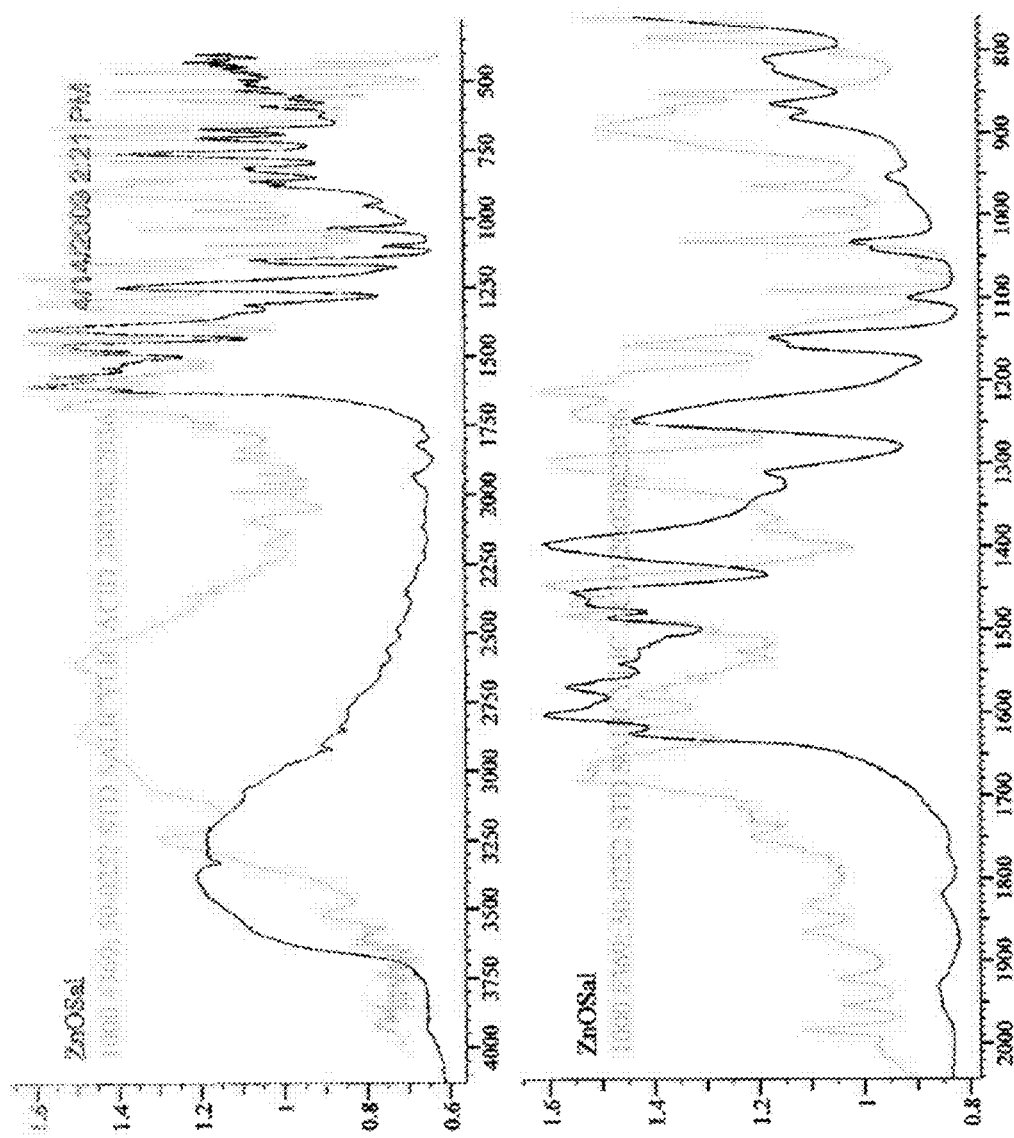
FIGS. 7E-F

ZINC OXIDE COMPLEXES

CROSS REFERENCE TO RELATED APPLICATIONS

This application is a continuation of U.S. patent application Ser. No. 15/499,478 filed Apr. 27, 2017, which is a divisional application of U.S. patent application Ser. No. 15/004,153 filed Jan. 22, 2016, now U.S. Pat. No. 9,657,036, which is a continuation of U.S. patent application Ser. No. 14/560,979, filed Dec. 4, 2014, now U.S. Pat. No. 9,273,071, which is a continuation of U.S. patent application Ser. No. 13/770,317, filed Feb. 19, 2013, now U.S. Pat. No. 8,933,257, which is a continuation of U.S. patent application Ser. No. 13/285,807, filed Oct. 31, 2011, now U.S. Pat. No. 8,404,743, which claims the benefit of U.S. Provisional Application No. 61/408,307, filed Oct. 29, 2010. The contents of the above-referenced applications are incorporated by reference.

BACKGROUND OF THE INVENTION

A. Field of the Invention

The present invention relates generally to compositions comprising zinc oxide complexes and methods for preparing such compositions.

B. Description of Related Art

Several skin treatment options are currently available for improving the visual appearance, physical properties, or physiological functions of the skin. Such options can be irritating to the skin, or the skin treatment formulation may be unstable. Thus, there is a need for skin treatment options that abate such undesirable characteristics.

SUMMARY OF THE INVENTION

The present invention overcomes deficiencies in the art by providing a compound comprising a first molecule and a second molecule, and corresponding methods of making and using the same. In some embodiments, the first molecule comprises an acidic hydrogen, and the second molecule comprises zinc oxide. While some molecules, such as acidic molecules can be irritating to the skin, zinc oxide molecules can counteract this undesirable effect by providing a soothing quality to skin. Further, both the acidic molecule and the zinc oxide molecule can impart benefits to skin and produce a synergistic complex. In some embodiments, the acidic molecule and zinc oxide molecule form a stable complex in aqueous, non-aqueous, low pH, high pH, high temperature, low temperature, humid, and dry storage environments.

In compounds of the invention, the molecule comprising zinc oxide may exist in a complex with one or more molecules comprising an acidic hydrogen. For example, the zinc oxide molecule may be complexed with one, two, three, or more molecules comprising an acidic hydrogen. In particular aspects, the zinc oxide molecule is complexed with one, two or three of the molecules comprising an acidic hydrogen. In some embodiments, the zinc oxide molecule is complexed with two molecules comprising an acidic hydrogen. For example, zinc oxide may complex with two lactic acid molecules to form a compound. In other embodiments, a molecule comprising an acidic hydrogen is complexed with one, two, three, or more molecules of zinc oxide. In yet further embodiments, two or more zinc oxide molecules are complexed with two or more molecules comprising an acidic hydrogen.

The molecule comprising an acidic hydrogen may be an organic molecule, such as an organic acid. In particular aspects, the molecule comprising an acidic hydrogen is a weak organic acid (as opposed to, for example, a strong mineral acid). In compounds of the invention, the zinc oxide molecule may be chemically bound to a chemical group containing an acidic hydrogen. For example, the molecule comprising an acidic hydrogen may be an alpha-hydroxy acid, and the zinc oxide molecule may chemically bind to the alpha-hydroxy group of the alpha-hydroxy acid, the organic acid group of the alpha-hydroxy acid, or both. In some embodiments, the zinc atom of the zinc oxide molecule chemically binds to the oxygen atom in a chemical group comprising at least one acidic hydrogen. In certain aspects, the oxygen atom of the zinc oxide molecule interacts with the acidic hydrogen of an —OH group, and the zinc molecule covalently bonds to the oxygen group of the acidic molecule. Although not wishing to be bound by any theory, in some embodiments, such an interaction can be illustrated as follows:

Step 1:

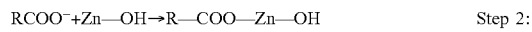

Step 2:

In step 1, the acidic hydrogen of the molecule comprising an acidic hydrogen attaches to the oxygen atom of zinc oxide, causing the zinc atom to shift to sp$^3$ hybrid orbitals. In step 2, the zinc then can accommodate the electron from the source of the acidic hydrogen (e.g., a caroboxylate ion).

It is contemplated that the methods disclosed herein can be used to form a compound comprising zinc oxide that is bound covalently or ionically to any molecule having an acidic hydrogen. Moreover, compositions disclosed herein may comprise zinc oxide that is bound covalently or ionically to any molecule having an acidic hydrogen. For example, in certain methods and compositions, the molecule comprising an acidic hydrogen may be a straight-chain aliphatic carboxylic acid, such as, for example, formic acid or stearic acid. In some embodiments, the molecule comprising an acidic hydrogen is a branched-chain aliphatic carboxylic acid, such as, for example, isobutyric acid (or 2-methylpropanoic acid) or pivalic acid (or 2,2-dimethylpropanoic acid).

In certain aspects, the molecule comprising an acidic hydrogen is a cyclic aliphatic carboxylic acid, such as, for example, cyclohexane carboxylic acid. Alternatively, the molecule comprising an acidic hydrogen may be a straight-chain olefinic carboxylic acid, such as, for example, acrylic acid or oleic acid. In some embodiments, compounds comprising zinc oxide and oleic acid, or salts thereof, are provided. In certain aspects, the compound consists of zinc oxide and oleic acid and has the following formula:

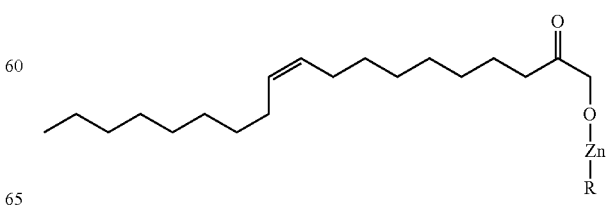

wherein R is O⁻ or OH.

In other aspects the molecule comprising an acidic hydrogen may be a branched-chain olefinic carboxylic acid, such as, for example, angelic acid (or Z-2-methyl-2-butenoic acid) or tiglic acid (or E-2-butenoic acid). The molecule comprising an acidic hydrogen may alternatively be a straight-chain polyunsaturated olefinic carboxylic acid, such as, for example, linoleic acid, linolenic acid, retinoic acid, or an omega-3 fatty acid. In some embodiments, the molecule comprising an acidic hydrogen is an aliphatic alpha-hydroxy acid, an aliphatic beta-hydroxy acid, an aliphatic delta-hydroxy acid, or an aliphatic gamma-hydroxy acid. In particular aspects, the molecule comprising an acidic hydrogen is an aliphatic alpha-hydroxy acid, such as, for example, lactic acid. In some embodiments, compounds comprising zinc oxide and lactic acid, and salts thereof, are provided. In certain aspects, a compound consisting of zinc oxide and lactic acid is provided having the following formula:

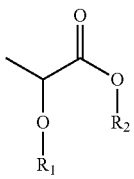

wherein $R_1$ is hydrogen or zinc oxide, $R_2$ is hydrogen or zinc oxide, and at least one of $R_1$ and $R_2$ is zinc oxide.

In certain embodiments, a compound comprising zinc oxide and lactic acid contains one zinc oxide molecule and two lactic acid molecules. In certain embodiments, a compound consisting of zinc oxide and lactic acid is provided having the following formula:

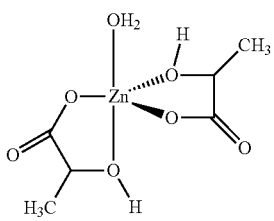

In other certain embodiments, a compound consisting of zinc oxide and lactic acid is provided having the following formula:

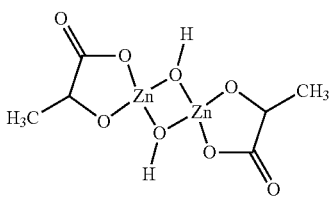

In yet other aspects, a compound consisting of zinc oxide and lactic acid has the following formula:

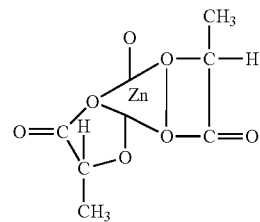

In certain aspects, compounds comprising zinc oxide and glycolic acid, and salts thereof, are provided. In some embodiments, a compound consisting of zinc oxide and glycolic acid is provided having the following formula:

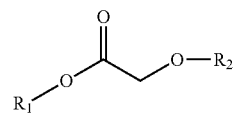

wherein $R_1$ is hydrogen or zinc oxide, $R_2$ is hydrogen or zinc oxide, and at least one of $R_1$ and $R_2$ is zinc oxide.

Also provided are complexes wherein the molecule comprising an acidic hydrogen is a vitamin comprising a carboxylic acid group. In some embodiments, the molecule comprising an acidic hydrogen is an aliphatic or olefinic di-acid. In other embodiments, the molecule comprising an acidic hydrogen is a dicarboxylic acid, such as, for example, azelaic acid, malic acid, adipic acid, or tartaric acid. For example, compounds comprising zinc oxide and azelaic acid, and salts thereof, are provided. In certain aspects, a compound consisting of zinc oxide and azelaic acid is provided having the following formula:

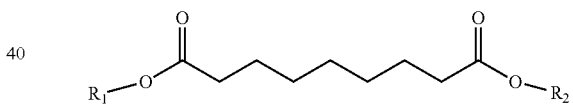

wherein $R_1$ is hydrogen or zinc oxide, $R_2$ is hydrogen or zinc oxide, and at least one of $R_1$ and $R_2$ is zinc oxide.

Also provided are compounds comprising zinc oxide and malic acid, and salts thereof. In certain aspects, a compound consisting of zinc oxide and malic acid is provided having the following formula:

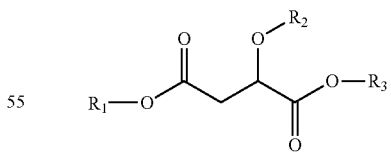

wherein $R_1$ is hydrogen or zinc oxide, $R_2$ is hydrogen or zinc oxide, $R_3$ is hydrogen or zinc oxide, and at least one of $R_1$, $R_2$, and $R_3$ is zinc oxide.

In some aspects, the molecule comprising an acidic hydrogen is a tri-acid, such as, for example, citric acid. For example, compounds comprising zinc oxide and citric acid, and salts thereof, are provided. In certain aspects, a compound consisting of zinc oxide and citric acid is provided having the following formula:

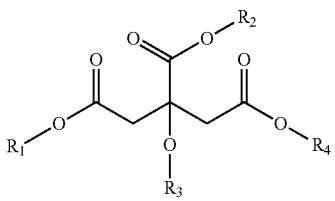

wherein $R_1$ is hydrogen or zinc oxide, $R_2$ is hydrogen or zinc oxide, $R_3$ is hydrogen or zinc oxide, $R_4$ is hydrogen or zinc oxide, and at least one of $R_1$, $R_2$, $R_3$, and $R_4$ is zinc oxide.

Also provided is a compound wherein the molecule having an acidic hydrogen is an amino acid, such as, for example, hydroxyproline. In particular aspects, compounds comprising zinc oxide and hydroxyproline, and salts thereof, are provided. In certain aspects, a compound consisting of zinc oxide and hydroxyproline is provided having the following formula:

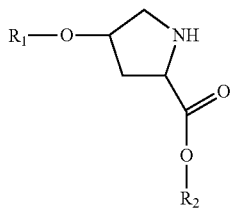

wherein $R_1$ is hydrogen or zinc oxide, $R_2$ is hydrogen or zinc oxide, and at least one of $R_1$ and $R_2$ is zinc oxide.

In some embodiments, the molecule comprising an acidic hydrogen is an aromatic acid, such as, for example, benzoic acid or salicylic acid. In some aspects, compounds comprising zinc oxide and salicylic acid, and salts thereof, are provided. In certain aspects, a compound consisting of zinc oxide and salicylic acid is provided having the following formula:

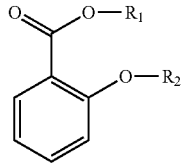

wherein $R_1$ is hydrogen or zinc oxide, $R_2$ is hydrogen or zinc oxide, and at least one of $R_1$ and $R_2$ is zinc oxide.

The molecule comprising an acidic hydrogen may be a substituted aromatic acid, such as, for example, para-aminobenzoic acid. Alternatively, the molecule comprising an acidic hydrogen may be an aromatic di-acid. In some embodiments, the aromatic di-acid is phthalic acid. In other embodiments, the molecule comprising an acidic hydrogen is an aromatic tri-acid, such as, for example, trimellitic acid.

In certain aspects, the molecule comprising an acidic hydrogen is ascorbic acid, a sugar acid, or mevalonic acid. In particular embodiments, the molecule comprising an acidic hydrogen is a sugar acid such as, for example gluconic acid. In other embodiments, the molecule having an acidic hydrogen is ascorbic acid. In such compounds, in certain embodiments, one of the hydrogen atoms from one or both of the hydroxyl groups is involved in forming the complex with zinc oxide. Compounds comprising zinc oxide and ascorbic acid, and salts thereof, are provided. In certain aspects, a compound consisting of zinc oxide and ascorbic acid is provided having the following formula:

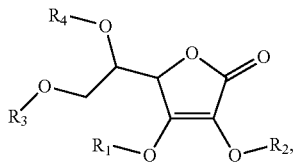

(II)

wherein $R_1$, $R_2$, $R_3$, or $R_4$ are each independently hydrogen or zinc oxide, provided that at least one of $R_1$, $R_2$, $R_3$, or $R_4$ is zinc oxide. In particular aspects, $R_1$ and $R_2$ are zinc oxide and $R_3$ and $R_4$ are H. In some aspects, $R_1$ or $R_2$ are zinc oxide and $R_3$, and $R_4$ are H. In still other aspects, $R_1$, and $R_2$ are H and $R_3$, and/or $R_4$ are zinc oxide. In one aspect, all of $R_1$, $R_2$, $R_3$, and $R_4$ are each zinc oxide. In one embodiment, $R_1$ is zinc oxide and each of $R_2$ $R_3$, and $R_4$ are H, or $R_2$ is zinc oxide and each of $R_1$ $R_3$, and $R_4$ are H, or $R_3$ is zinc oxide and each of $R_1$ $R_2$, and $R_4$ are H, or $R_4$ is zinc oxide and each of $R_1$ $R_2$, and $R_3$ are H.

The molecule comprising an acidic hydrogen may be a thio-acid, such as, for example, thioglycolic acid or thiolactic acid. In other embodiments, the molecule having an acidic hydrogen is a beta-diketone, such as, for example, avobenzone. Compositions comprising zinc oxide and avobenzone, and salts thereof, are provided. In a particular embodiment, the zinc oxide molecule is chemically bound to one of the methylene group hydrogens of the avobenzone molecule. In certain aspects, a compound consisting of zinc oxide and avobenzone is provided having the following formula:

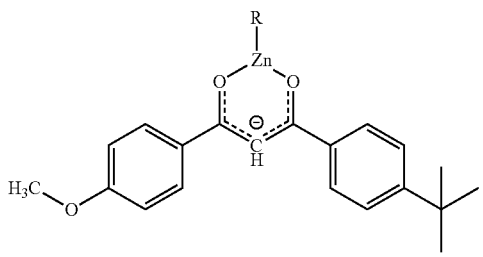

wherein R is O⁻ or OH.

In particular embodiments, the molecule comprising an acidic hydrogen is dihydroxyacetone. In other embodiments, the molecule comprising an acidic hydrogen is phenol or a substituted phenol. Compounds comprising zinc oxide and phenol, and salts thereof, are provided. In certain aspects, a compound consisting of zinc oxide and phenol is provided having the following formula:

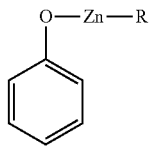

wherein R is O⁻ or OH.

Also provided are compounds wherein the molecule comprising an acidic hydrogen is a steroid. In yet further aspects, the molecule comprising an acidic hydrogen has at least one acidic hydrogen located alpha to a: ketone, double bond, benzene ring, ether, or carboxylic acid. In still further aspects, the molecule comprising an acidic hydrogen is a vulcanizing accelerator, such as, for example, a disulfide, dithiocarbamate, thiuram, mercaptobenzothiazole, or alkylphenoldisulfide.

In some embodiments, the molecule comprising an acidic hydrogen is pyrithione or anthralin (or dithranol). In certain aspects, the molecule comprising an acidic hydrogen is Kojic acid. Compounds comprising zinc oxide and Kojic acid, and salts thereof, are provided. In certain embodiments, a compound consisting of zinc oxide and Kojic acid is provided having the following formula:

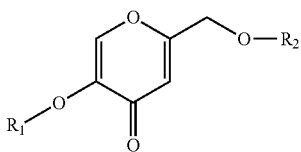

wherein $R_1$ is hydrogen or zinc oxide, $R_2$ is hydrogen or zinc oxide, and at least one of $R_1$ and $R_2$ is zinc oxide.

In some embodiments, the molecule comprising an acidic hydrogen is cyclic unsaturated olefinic carboxylic acid.

Also provided are methods for chemically binding a zinc molecule to a molecule comprising an acidic hydrogen comprising: (a) mixing the zinc molecule and the molecule comprising an acidic hydrogen in a liquid comprising at least about 80% by weight alcohol; and (b) mixing the zinc molecule and the molecule comprising an acidic hydrogen in a sealed container, wherein the zinc molecule covalently bonds to the molecule comprising an acidic hydrogen. For example, the zinc molecule may be zinc oxide, and the chemical bond may be a covalent bond. It is contemplated that the methods disclosed herein can be used to chemically bond a zinc molecule, such as zinc oxide, to any molecule having an acidic hydrogen.

In certain embodiments of the provided methods, the mixing of the zinc molecule and the molecule comprising an acidic hydrogen is in a liquid comprising at least about 85% by weight alcohol, at least about 90% by weight alcohol, at least about 95% by weight alcohol, at least about 100% by weight alcohol, or any percentage derivable therein. In some embodiments, the mixing of the zinc molecule and the molecule comprising an acidic hydrogen is in a liquid that is free or essentially free of water. In other embodiments, the mixing of the zinc molecule and the molecule comprising an acidic hydrogen is in a liquid that is an anhydrous alcohol. In certain aspects, the mixing of the zinc molecule and the molecule comprising an acidic hydrogen is in a liquid containing one or more reagent-grade alcohols or one or more denatured alcohols. In particular aspects, the mixing of the zinc molecule and the molecule comprising an acidic hydrogen is in a liquid comprising ethanol, methanol, or isopropanol, or a combination of two or more of these. In yet further aspects, the mixing of the zinc molecule and the molecule comprising an acidic hydrogen is in a liquid comprising a nitrogen-free alcohol. In still further aspects, the mixing occurs in acetone.

In some embodiments, the zinc molecule and the molecule comprising an acidic hydrogen are mixed in about a 1:1 molar ratio of zinc molecules to molecule comprising an acidic hydrogens or in about a 2:1 molar ratio of zinc molecules to molecules comprising an acidic hydrogen. In particular aspects, about 1 gram of zinc oxide is mixed with a molecule comprising an acidic hydrogen in about a 1:1 molar ratio. In some aspects of the disclosed methods, zinc oxide is mixed with a molecule comprising an acidic hydrogen in about 200-250 mL of a liquid comprising more than about 80% by weight alcohol.

The zinc molecule and molecule comprising an acidic hydrogen may be mixed for about 5 to about 60 days. For example, the molecules may be mixed for about 5 to about 10 days, for about 10 to about 20 days, for about 20 to about 30 days, for about 30 to about 40 days, for about 40 to about 50 days, for about 50 to about 60 days, or any range derivable therein. In certain aspects, the zinc molecule and molecule comprising an acidic hydrogen are mixed in a sealed glass container. In some embodiments, the zinc molecule and molecule comprising an acidic hydrogen are mixed in an opaque container.

The zinc molecule and molecule comprising an acidic hydrogen may be mixed by, for example, stirring, vortexing, sonicating, or shaking. Stirring may be performed using a magnetic stirrer. In certain embodiments, the mixture containing the zinc molecule and molecule comprising an acidic hydrogen is heated during at least part of the mixing time. For example, a composition comprising a zinc molecule and a molecule comprising an acidic hydrogen may be heated to the reflux temperature for the alcohol in the composition.

In some aspects, complexes between one or more zinc molecules chemically bound to one or more molecules comprising an acidic hydrogen are isolated. Such complexes may comprise a compound wherein the zinc molecule is covalently bound to the molecule comprising an acidic hydrogen. Means of isolating the complexes include, for example, filtering, evaporation, rotary evaporation, drying, spray drying, centrifugation, or precipitation. In certain embodiments, the complexes comprising one or more zinc molecules covalently bound to one or more molecules comprising an acidic hydrogen are crystals. A crystal is a solid material having constituent parts (atoms, molecules, or ions) that are arranged in an orderly repeating pattern. Complexes disclosed herein that are in crystal form may be isolated by filtering.

Complexes comprising one or more zinc molecules chemically bound to one or more molecules comprising an acidic hydrogen may be stored. For example, the complexes may be stored at a temperature between about 10 degrees C. to about −30 degrees C.

In some embodiments, complexes comprising one or more zinc molecules chemically bound to one or more molecules comprising an acidic hydrogen have a melting point greater than about 30 degrees C. to about 200 degrees C. In some aspects, the complexes comprising one or more zinc oxide molecules chemically bound to one or more molecules comprising an acidic hydrogen have a melting point greater than about 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees C., or any temperature derivable therein. Complexes comprising one or more zinc molecules chemically bound to one or more molecules comprising an acidic hydrogen may have a melting point greater than about 120 degrees C. to about 140 degrees C. In certain embodiments, the complex comprising one or more zinc molecules chemically bound to one or more molecules comprising an acidic hydrogen has a melting point that is greater than the melting point for the molecule comprising an acidic hydrogen substituent of the complex. In the case of some complexes comprising one or more zinc molecules chemically bound to one or more liquid molecules comprising an acidic hydrogen (such as lactic acid, for example), the complexes exhibit no melting point at temperatures up to about 175 degrees C. to about 200 degrees C. In certain aspects, the complexes comprising one or more zinc molecules chemically bond to one or more molecules comprising an acidic hydrogen dissociate in an aqueous composition.

In particular aspects of the disclosed methods, complexes between zinc oxide and an organic molecule are provided. In some embodiments, the organic molecule is an organic acid. In certain aspects, the organic molecule is: ascorbic acid, avobenzone, lactic acid, glycolic acid, oleic acid, hydroxyproline, azelaic acid, salicylic acid, citric acid, malic acid, Kojic acid, or phenol. Such compounds may be provided in crystal form.

The compounds provided herein may be provided in a composition. For example, a composition is provided comprising any of the compounds provided herein, or, in certain aspects, a composition is provided that can include at least two or more of the compounds provided herein. It should be recognized that the amount of a compound provided herein within a composition can be selected based on the desired results. The amount of such ingredients can include less than 0.0001% or can include 0.0001, 0.0002 . . . 0.002, 0.003, 0.004 . . . 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more or, or any range derivable therein, by weight or volume of any of the compounds disclosed herein.

It is contemplated that the compounds, compositions, and methods disclosed herein may have many uses. For example, provided are topical skin compositions that include one or more of the compounds or compositions disclosed herein. Also provided are pharmaceutical compositions that include one or more of the compounds or compositions disclosed herein. In some embodiments, the methods disclosed herein are used to provide a topical skin composition or a pharmaceutical composition.

In certain embodiments, the compositions are formulated into topical skin care compositions. The compositions can be cosmetic compositions or pharmaceutical compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, skin-whitening/lightening, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). In particular embodiments, the composition has a viscosity ranging from 14,000 to 30,000 cps. The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In particular aspects, the compositions can be oil-free, substantially anhydrous, and/or anhydrous. Other aspects include compositions having water.

In some embodiments, methods for making compounds are provided comprising: (a) mixing a zinc molecule and a molecule comprising an acidic hydrogen in a liquid comprising at least about 80% by weight alcohol; (b) mixing the zinc molecule and the molecule comprising an acidic hydrogen in a sealed container, wherein the zinc molecule bonds to the molecule comprising an acidic hydrogen. Also provided are compounds, such as the compounds disclosed herein, prepared by a process comprising the steps of: (a) mixing a zinc molecule and a molecule comprising an acidic hydrogen having an acidic hydrogen in a liquid comprising at least about 80% by weight alcohol; (b) mixing the zinc molecule and the molecule comprising an acidic hydrogen in a sealed container, wherein the zinc molecule bonds to the molecule comprising an acidic hydrogen. A bond between the zinc molecule and the molecule comprising an acidic hydrogen may be covalent or ionic.

In yet another embodiment, there is disclosed a process for making a compound of formula:

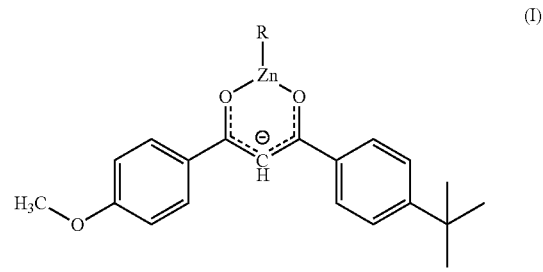

(I)

wherein R is O⁻ or OH, or

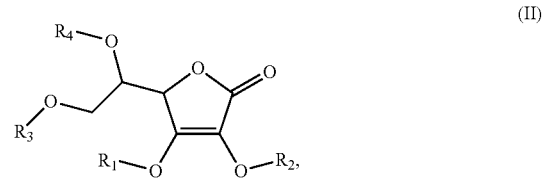

(II)

wherein $R_1$, $R_2$, $R_3$, or $R_4$ are each independently hydrogen or zinc oxide, provided that at least one of $R_1$, $R_2$, $R_3$, or $R_4$ is zinc oxide, comprising mixing a zinc oxide and a molecule having the formula:

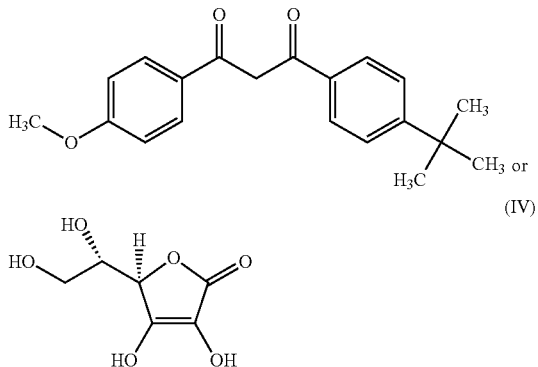

(III)

(IV)

in a liquid to form a substantially anhydrous mixture, wherein said liquid comprises at least 80% by weight of alcohol in said liquid; and obtaining from the mixture a compound of formula (I) or formula (II). In certain aspects, $R_1$, $R_2$, $R_3$, or $R_4$ on the zinc oxide/ascorbic acid complex are each independently hydrogen or zinc oxide, provided that at least one of $R_1$, $R_2$, $R_3$, or $R_4$ is zinc oxide. In particular aspects, $R_1$ and $R_2$ are zinc oxide and $R_3$ and $R_4$ are H. In some aspects, $R_1$ or $R_2$ are zinc oxide and $R_3$, and $R_4$ are H. In still other aspects, $R_1$, and $R_2$ are H and $R_3$, and/or $R_4$ are zinc oxide. In one aspect, all of $R_1$, $R_2$, $R_3$, or $R_4$ are each zinc oxide. In one embodiment, $R_1$ is zinc oxide and each of $R_2$ $R_3$, or $R_4$ are H, or $R_2$ is zinc oxide and each of $R_1$ $R_3$, and $R_4$ are H, or $R_3$ is zinc oxide and each of $R_1$ $R_2$, and $R_4$ are H, or $R_4$ is zinc oxide and each of $R_1$ $R_2$, and $R_3$ are H. In addition to avobenzone and ascorbic acid, other molecules having acidic hydrogen can be used in this process (e.g., lactic acid, glycolic acid, oleic acid, hydroxyproline, azaleic acid, salicylic acid, etc.), which would result in the compounds disclosed throughout this specification, identified in the figures, and illustrated in the Examples. In particular, aspects, the alcohol can be methanol, ethanol, propanol, or isopropanol, or mixtures thereof. The molar ratio of the zinc oxide and the molecules having an acidic hydrogen present in the mixture can be at a molar ratio of about 1:1 to about 2:1. The mixture can be mixed at room temperature (which is approximately about 20° C. to about 25° C.). Alternatively, heat can be used to speed up the reaction process. In particular aspects, the mixture can be mixed for 7 to 21 days at room temperature. The resulting or produced compound can be isolated by filtration followed by air-drying, evaporation, or spray-drying the filtered substance (filtrate). The resulting or produced compound can be in crystal form, semi-crystalline form, or amorphous form. The alcohol can be present within the liquid at amounts of at least 80, 85, 90, 95, 99, to 100%. In certain aspects, a co-solvent can be used to assist in solubilizing the molecule having an acidic hydrogen within the mixture. The mixture can consist of zinc oxide, the molecule having an acidic hydrogen, and an alcohol (or mixture of alcohols). The mixture can consist of zinc oxide, the molecule having an acidic hydrogen, an alcohol, and/or a co-solvent (e.g., toluene).

Further, the processes of mixing zinc oxide with a molecule having an acidic hydrogen can also result in a polymeric chain of alternating zinc oxide monomers with a molecule having an acidic hydrogen. For instance, if "A" represents zinc oxide and "B" represents the molecule having an acid hydrogen, then the polymeric structure would be AB/AB/AB . . . . The link between A and B would take place between zinc and the oxygen from the hydroxyl group of the acid hydrogen.

In certain aspects, methods of treating or preventing a skin condition are provided. For example, any of the compounds disclosed herein may be useful in methods of treating or preventing a skin condition. In particular aspects, a method of treating or preventing a skin condition is provided using a compound comprising at least one zinc molecule chemically bound to at least one molecule comprising an acidic hydrogen, wherein the compound is prepared by a process comprising the steps of: (a) mixing a zinc molecule and a molecule comprising an acidic hydrogen having an acidic hydrogen in a liquid comprising at least about 80% by weight alcohol; (b) mixing the zinc molecule and the molecule comprising an acidic hydrogen in a sealed container, wherein the zinc molecule bonds to the molecule comprising an acidic hydrogen. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. In particular aspects, the skin condition to be treated may be dry skin, rash, acne, poison ivy, skin irritation, a wound, a freckle, a sunspot, an age spot, skin discoloration, fine lines, wrinkles, hyperpigmentation, or dandruff.

The skin treated can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin). In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

In other aspects, methods of protecting a surface against ultraviolet radiation are provided. For example, a surface may be protected against ultraviolet radiation by applying to the surface any of the compounds disclosed herein. In certain embodiments, a method of protecting a surface against ultraviolet radiation is provided using a composition that contains a compound comprising at least one zinc molecule covalently bound to at least one molecule comprising an acidic hydrogen, wherein the compound is prepared by a process comprising the steps of: (a) mixing a zinc molecule and a molecule comprising an acidic hydrogen having an acidic hydrogen in a liquid comprising at least about 80% by weight alcohol; (b) mixing the zinc molecule and the molecule comprising an acidic hydrogen in a sealed container, wherein the zinc molecule bonds to the molecule comprising an acidic hydrogen. In some embodiments, the surface to be protected from ultraviolet radiation is skin, wood, plastic, glass, or metal.

Also provided are compositions for protecting a surface against ultraviolet radiation. For example, such compositions may comprise a compound comprising at least one zinc molecule covalently bound to at least one molecule comprising an acidic hydrogen, wherein the compound is prepared by a process comprising the steps of: (a) mixing a zinc molecule and a molecule comprising an acidic hydrogen having an acidic hydrogen in a liquid comprising at least about 80% by weight alcohol; (b) mixing the zinc molecule and the molecule comprising an acidic hydrogen in a sealed container, wherein the zinc molecule bonds to the molecule comprising an acidic hydrogen. Also, a composition for protecting a surface against ultraviolet radiation my comprise any of the compounds disclosed herein. Compositions for protecting a surface against ultraviolet radiation may comprise a topical skin composition, a cosmetic, a paint, an adhesive, an ointment, a sealant, a tape, a film, a spray, a cleanser, a physical sunblock composition, a chemical sunblock composition, a gel, or a polish.

Pharmaceutical compositions and methods for making a pharmaceutical composition are provided. In some embodiments, the pharmaceutical composition comprises a liquid, a gel, a capsule, a spray, an aerosol, a tablet, or a lozenge. Pharmaceutical compositions may be administered by topical, oral, nasal, buccal, rectal, or vaginal means. In certain embodiments, a pharmaceutical composition is administered by intravenous, intraspinal, intracerebral, intradermal, subcutaneous, intramuscular, or intraperitoneal methods.

In some embodiments, a composition comprising a compound disclosed herein comprises a sunscreen, an exfoliating composition, a chemical peel, a moisturizer, a silicone-containing composition, a skin-calming composition, an ointment, a cream, a cleanser, an anhydrous composition, an antimicrobial composition, an antifungal composition, an astringent, a cosmetic, a cosmetic foundation, a powder, a water-resistant composition, a wound-healing composition, a skin-whitening composition, a perfume, an anti-inflammatory composition, a deodorizing composition, or an antiperspirant.

Also contemplated are kits that include compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product or a pharmaceutical product. The cosmetic product or pharmaceutical product can be those described in other sections of this specification or those known to a person of skill in the art. Non-limiting examples of cosmetic products include a moisturizer, a cream, a lotion, a skin softener, a foundation, a night cream, a lipstick, a cleanser, a toner, a sunscreen, a mask, or an anti-aging product. Non-limiting examples of pharmaceutical products include a liquid, a gel, a capsule, a spray, an aerosol, a tablet, or a lozenge.

In certain embodiments, methods for preparing a compound comprising zinc oxide and ascorbic acid are provided. In certain embodiments, the zinc oxide and ascorbic acid are mixed in a liquid comprising at least about 80% by weight alcohol comprises nitrogen-free alcohol. In certain aspects, the mixing is performed under a nitrogen blanket. The sealed container may be an opaque container. The zinc oxide and ascorbic acid molecules may be mixed for about 7 days to about 21 days, or they may be mixed for about 14 days to about 28 days.

In some aspects, methods for preparing a compound comprising zinc oxide and avobenzone are provided. In certain embodiments, the zinc oxide and avobenzone molecules from particulate complexes comprising zinc oxide and avobenzone. Such complexes may be isolated by, for example, filtering. In particular aspects, the complexes containing zinc oxide and avobenzone exhibit a melting point greater than about 80 degrees C.

Also provided are methods for preparing a compound comprising zinc oxide and lactic acid. For example, in certain aspects, the zinc oxide and lactic acid molecules are mixed for about 7 days to 21 days. In some embodiments, the zinc oxide and lactic acid molecules form particulate complexes comprising zinc oxide and lactic acid. Complexes comprising zinc oxide and lactic acid may be isolated by methods such as, for example, filtering. In certain embodiments, the complexes comprising zinc oxide and lactic acid dissociate in an aqueous solution. In particular aspects, the complexes containing zinc oxide and lactic acid exhibit a melting point greater than about 53 degrees C.

In some embodiments, methods for preparing a compound comprising zinc oxide and glycolic acid are provided. In certain aspects, the methods provide for the formation of particulate complexes comprising zinc oxide and glycolic acid. Such particulate complexes may be isolate by methods such as, for example, filtering.

In particular embodiments, methods for preparing a compound comprising zinc oxide and oleic acid are provided. The zinc oxide and oleic acid molecules may be mixed for about 14 days to about 28 days. The zinc oxide and oleic acid molecules, in certain embodiments, form particulate complexes comprising zinc oxide and oleic acid. Such complexes may be isolated by methods such as, for example, filtering.

Also provided are methods for preparing a compound comprising zinc oxide and hydroxyproline. In certain aspects, the zinc oxide and hydroxyproline molecules are mixed in a liquid comprising at least about 80% by weight alcohol comprises. The alcohol may be an anhydrous alcohol. In some embodiments, the zinc oxide and hydroxyproline molecules form particulate complexes comprising zinc oxide and hydroxyproline. Such complexes may be isolated by methods such as, for example, filtering. In some aspects, the zinc oxide and hydroxyproline molecules are mixed for about 7 days to about 21 days.

In some embodiments, methods are provided for preparing a compound comprising zinc oxide and azelaic acid. In certain aspects, the zinc oxide and azelaic acid molecules form complexes comprising zinc oxide and azelaic acid. Such complexes may exhibit a melting point greater than about 104 degrees C.

Provided are methods for preparing a compound comprising zinc oxide and salicylic acid. In certain aspects of such methods, the zinc oxide and salicylic acid molecules form particulate complexes comprising zinc oxide and salicylic acid. Such complexes may be isolated by methods such as, for example, filtering. In some embodiments, complexes comprising zinc oxide and salicylic acid exhibit a melting point greater than about 159 degrees C.

Also provided are methods for preparing a compound comprising zinc oxide and citric acid. In particular aspects, the zinc oxide and citric acid molecules are mixed in about a 1:1 molar ratio of zinc molecules to citric acid molecules. In other aspects, the zinc oxide and citric acid molecules are mixed in about a 2:1 molar ratio of zinc molecules to citric acid molecules. The zinc oxide and citric acid molecules may form particulate complexes comprising zinc oxide and citric acid. Such complexes may be isolated by methods such as, for example, filtering.

It is contemplated that the compositions comprising compounds disclosed herein may deliver an active agent. In some embodiments, the active agent is a vitamin, an acid, an antioxidant, or a medicament. For example, in certain embodiments, complexes of the present invention are used to deliver an alpha-hydroxy acid, lactic acid, azelaic acid, salicylic acid, glyceryl salicylate, ascorbic acid, zinc, or zinc oxide.

In some aspects, a complex is providing having the formula $ZnO.CH_3(CH_2)_7CH = CH(CH_2)_7COOH$. In other aspects, a complex is provided having the formula $ZnO.CH_3CH(OH)COOH$, having the formula $ZnO.2(CH_3CH(OH)COOH)$, having the formula $ZnO.HOCH_2COOH$, having the formula $ZnO.HOOC(CH_2)_7COOH$, having the formula $ZnO.HOOCCH_2CHOHCOOH$, having the formula $ZnO.HOC(COOH)(CH_2COOH)_2$, having the formula $2(ZnO).HOC(COOH)(CH_2COOH)_2$, having the formula $ZnO.OC1CNC(C1)C(O)=O$, having the formula $ZnO.C6H4(OH)COOH$, having the formula $ZnO.2(C6H4(OH)COOH)$, having the formula $ZnO.C(C(C1C(=O)C(=C(O1)O)O)O)O$, having the formula $ZnO.CC(C)(C)C1=CC=C(C=C1)C(=O)CC(=O)C2=CC=C(C=C2)OC$, having the formula $ZnO.C1=CC=C(C=C1)O$, or having the formula $ZnO.C1=C(OC=C(C1=O)O)CO$. Any such complex or any complex disclosed herein may be in crystalline form, semi-crystalline form, or amorphous form.

It is also contemplated that complexes disclosed herein may aid in the process of vulcanization of rubber or prevulcanization of liquid latex rubber. Vulcanization is a chemical process that converts rubber or related polymers into more durable materials, such as by the addition of sulfur or similar components. Vulcanized materials are desirable because of their improved properties, such as decreased stickiness and improved mechanical properties. Many products are made using vulcanized rubber, such as tires, shoe sole, and hoses. In some embodiments, complexes comprising zinc oxide and a vulcanizing accelerator (e.g., disulfides, dithiocarbamates, thiurams, alkylphenoldisulfides, or any other vulcanizing accelerator known to those of skill in the art) are provided. In some embodiments, such complexes may be used to aid in the vulcanization process by delivering the vulcanizing accelerator to the process or by improving the ability of the vulcanizing accelerator to catalyze the vulcanization. Also provided are methods of using such complexes to accelerate vulcanization.

The invention also provides compounds comprising a first molecule comprising an acidic hydrogen and a second molecule comprising an amphoteric oxide other than zinc oxide. The amphoteric oxide other than zinc oxide may be calcium oxide, magnesium oxide, iron oxide, copper oxide, and cobalt oxide. In yet other embodiments, the invention provides compounds comprising a first molecule comprising an acidic hydrogen and a second molecule comprising zinc. For example, the second molecule comprising zinc may be zinc nitrate, zinc nitrite, or a molecule containing zinc nitrate or zinc nitrite.

Some chemical formulas used herein are provided in simplified molecular input line entry specification (SMILES) format. SMILES is a specification that unambiguously describes the structure of chemical molecules. Use of SMILES to describe chemical molecules is known to those of ordinary skill in the art.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

As used herein, the terms "bond" or "bound" refer to a chemical bond between two molecules and include covalent or ionic bonds.

As used herein, the terms "compound" or "complex" refer to the resulting structure or association that is obtained when two or more molecules are linked together via one or more chemical bonds.

As used herein, the term "acidic molecule" includes any molecule that has an acidic hydrogen. The term "acidic hydrogen" refers to a substance that donates one ore more hydrogen ions to another substance, or a substance in which a hydrogen atom can be removed from the substance by a base (e.g., sodium hydroxide, amines, etc.). One or more "acidic hydrogens" within a given molecule can be bonded to carbon, oxygen, nitrogen, sulfur or any other element in the Periodic Table of the Elements.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002)

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%. Thus, a composition that is substantially anhydrous has less than 10%, less than 5%, less than 1%, or less than 0.5% by weight of the composition or mixture of water. An anhydrous composition or mixture (which is also contemplated as being useful in the context of the present invention) can also be used and would have no water.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

The compositions of the invention can comprise, consist essentially of, or consist of the claimed ingredients. In one aspect, compositions consisting essentially of the claimed ingredients excludes ingredients that would materially affect one or more of a given composition's desired characteristics, such as the ability to firm skin, increase the elasticity of skin, stimulate dermal or epidermal cellular activity of skin to increase the connection between the dermal and epidermal layers, reduce or prevent free-radical damage or oxidative damage of skin, moisturize skin, protect a surface from ultraviolet radiation, and/or reduce or prevent dry skin or flaky skin.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

FIGS. 2A-C: Infrared data concerning a zinc oxide/azaleic acid compound.

FIGS. 3A-C: Infrared data concerning a zinc oxide/avobenzone compound.

FIGS. 4A-C: Infrared data concerning a zinc oxide/oleic acid compound.

FIGS. 6A-C: Infrared data concerning a zinc oxide/lactic acid compound.

FIGS. 7A-F: Infrared data concerning a zinc oxide/salicylic acid compound.

DESCRIPTION OF ILLUSTRATIVE EMBODIMENTS

Figure 1:
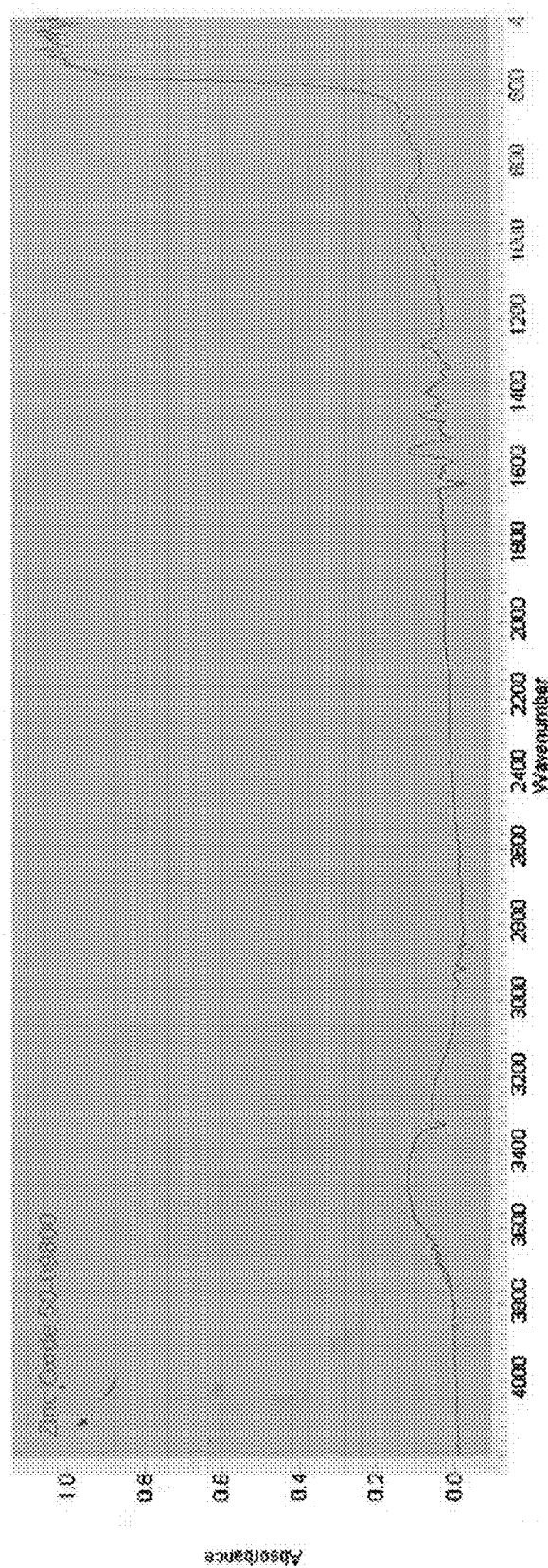
FIG. 1: Infrared data concerning Zinc Oxide.

Acidic molecules, such as molecules containing an acidic hydrogen, have many beneficial properties. For example, such molecules may act as exfoliants, acne treatments, sunscreens, wrinkle treatments, or discoloration treatments. Thus, acidic molecules may be useful in many topical skin compositions or pharmaceutical compositions. However, despite all of the beneficial properties of acidic molecules, such molecules can cause irritation to the skin.

Zinc oxide has many beneficial properties including its antibacterial, antifungal, anti-inflammatory, skin-calming, and UV-protection properties. Thus, zinc oxide may be useful in many topical skin compositions or pharmaceutical compositions. For example, zinc oxide may be useful in compositions that contain acidic molecules, where the skin-soothing properties of zinc oxide can counteract the undesirable skin-irritating effects of the acidic molecules.

The present invention overcomes deficiencies in the prior art by providing stable compounds that contain zinc oxide chemically bound to a molecule comprising an acidic hydrogen. Such compounds provide advantages over prior art compounds because the compounds of the present invention are stable in a variety of environments such as aqueous, non-aqueous, low pH, high pH, high temperature, low temperature, humid, and dry storage environments. In addition, compounds comprising zinc oxide chemically bound to a molecule having an acidic hydrogen are beneficial over the prior art in that such compounds allow one to readily control the ratio of zinc oxide molecules to molecules having an acidic hydrogen. Finally, the compounds of the present invention allow a zinc oxide molecule to be delivered with each molecule comprising an acidic hydrogen, thus ensuring that the skin-soothing effects of zinc oxide are provided at the precise location where skin-soothing properties are needed.

A. Compounds

In certain aspects, compounds containing one or more zinc molecules and one or more molecules comprising an acidic hydrogen are provided, as well as salts thereof. For example, compounds containing one or more zinc oxide molecules covalently or ionically bound to one or more acidic molecules are provided. In particular embodiments, zinc oxide is covalently bound to a molecule comprising an acidic hydrogen. The invention also provides effective methods for producing such compounds and compositions comprising one or more of such compounds.

As will be clear from the present disclosure, compounds and compositions of the invention have numerous uses, such as, but not limited to, in topical skin compositions, in pharmaceutical compositions, as delivery vehicles for active agents, or in methods for treating a skin conditions or protecting a surface from ultraviolet radiation.

1. Zinc Molecules

Zinc is a metallic chemical element with the symbol Zn and atomic number 30. Zinc is an essential mineral, and zinc deficiency affects about two billion people in the developing world and is associated with many diseases. Enzymes with a zinc atom in the reactive center are common, such as alcohol dehydrogenase.

In some embodiments, the zinc molecule is zinc oxide. Zinc oxide has the chemical formula ZnO. It is nearly insoluble in neutral aqueous solutions. Compositions containing zinc oxide may be useful as antibacterial compositions, for protection from ultraviolet radiation, as ointments (e.g., for soothing skin irritation), as calamine lotions, in restorative or prosthodontic compositions, as deodorants, as packing materials, in baby powders, in barrier creams, in anti-dandruff compositions, as antiseptics, as components of athletic tapes, in sunscreen compositions, in anti-inflammatory compositions, as components of filters (e.g., cigarette filters), as food additives, as dietary supplements, as pigments (e.g., in paints or topical skin formulations), or as coatings (e.g., an anti-corrosive coating), among other uses that are known to one of skill in the art.

Compositions that contain zinc oxide may include topical skin formulations, pharmaceutical compositions, plastics, ceramics, glass, cement, rubber, lubricants, paints, ointments, adhesives, sealants, pigments, foods, batteries, ferrites, and fire retardants, among others.

When used as an ingredient in sunscreen, zinc oxide sits on the skin's surface rather than being absorbed into the skin. Zinc oxide blocks both UVA (320-400 nm) and UVB (280-320 nm) rays of ultraviolet light. Because zinc oxide is not absorbed into the skin, it is non-irritating and non-allergenic. Zinc oxide can be used in ointments, creams, lotions, and sprays to protect against sunburn and other damage to the skin caused by ultraviolet light.

Zinc oxide coatings may be used for energy-saving or heat-protecting windows. The coating allows the visible part of the spectrum to pass through while reflecting infrared (IR) radiation back into the room (energy saving) or preventing the IR radiation from entering the room (heat protecting), depending on which side of the window has the coating. Zinc oxide coatings may also be used to protect plastics, such as polyethylene naphthalate (PEN). Zinc oxide can also be used to coat polycarbonate (PC) to protect it from solar radiation and decrease its rate of oxidation and photoyellowing.

2. Acidic Molecules

Molecules comprising an acidic hydrogen, also referred to herein as acidic molecules, have many beneficial properties, as discussed throughout the specification. Such benefits include, but are not limited to, the following properties: exfoliating, anti-aging, wrinkle-treating, discoloration-treating, anti-acne, antibacterial, and antifungal properties.

Acidic molecules useful in the invention include, but are not limited to, cyclic aliphatic carboxylic acids (e.g., cyclohexane carboxylic acid, straight-chain olefinic carboxylic acids (e.g., acrylic acid, oleic acid). branched-chain olefinic carboxylic acids (e.g., angelic acid (or Z-2-methyl-2-butenoic acid), tiglic acid (or E-2-butenoic acid)), straight-chain polyunsaturated olefinic carboxylic acids (e.g., linoleic acid, linolenic acid, retinoic acid, an omega-3 fatty acid), aliphatic alpha-hydroxy acids (e.g., lactic acid), aliphatic beta-hydroxy acids, aliphatic delta-hydroxy acids, aliphatic gamma-hydroxy acids, glycolic acid, vitamins comprising a carboxylic acid group, aliphatic or olefinic di-acids, dicarboxylic acids (e.g., azelaic acid, malic acid, adipic acid, tartaric acid), tri-acids (e.g., citric acid), amino acids (e.g., hydroxyproline), aromatic acids (e.g., benzoic acid, salicylic acid), substituted aromatic acids (e.g., para-aminobenzoic acid), aromatic di-acids (e.g., phthalic acid), aromatic tri-acids (e.g., trimellitic acid), ascorbic acid, a sugar acid (e.g., gluconic acid), mevalonic acid, thio-acids (e.g., thioglycolic acid, thiolactic acid), beta-diketones (e.g., avobenzone), dihydroxyacetone, phenols, substituted phenols, steroids, vulcanizing accelerators (e.g., disulfides, dithiocarbamates, thiurams, alkylphenoldisulfides), pyrithione, anthralin (or dithranol), Kojic acid, or cyclic unsaturated olefinic carboxylic acids. A molecule comprising an acidic hydrogen may also be any molecule that has at least one acidic hydrogen located alpha to a: ketone, double bond, benzene ring, ether, or carboxylic acid.

B. Methods of Making Compounds

Also provided are methods for producing a compound comprising a molecule comprising zinc oxide that is chemically bound to a molecule comprising an acidic hydrogen. Most commonly, the molecule comprising an acidic hydrogen is a weak organic acid (as opposed to, for example, a strong mineral acid).

The formation of a complex between zinc oxide and the molecule comprising an acidic hydrogen (e.g., an acidic organic compound) can be confirmed by infrared (IR) spectroscopy. For example, formation of the complex is indicated by an IR spectrum that exhibits a combination of the IR spectrum of zinc oxide and the IR spectrum of the molecule comprising an acidic hydrogen (e.g., the particular acidic organic compound used).

Zinc oxide complexes may be formed in an alcohol solution, such as an ethanol solution, containing approximately 20% or less water. In some embodiments, the solution contains approximately 10% or less water. Suitable alcohols include but are not limited to ethanol, anhydrous reagent grade alcohol, methanol, isopropanol, butanol, octanol, or any such alcohol known to those of skill in the art. Moreover, zinc oxide complexes may be formed in a solvent solution that does or does not contain alcohol. Suitable solvents include but are not limited to toluene, hexanes, acetone, or any such solvent known to those of skill in the art. Mixing may occur in any combination of such alcohols or solvents and may vary depending on how much of a particular alcohol or other solvent is needed to help solubilize the components of the zinc oxide complex.

The zinc oxide molecule and the molecule comprising an acidic hydrogen (such as an organic compound or organic acid) may be weighed in a 1:1 molar ratio. In other embodiments, the zinc oxide molecule and the molecule comprising an acidic hydrogen are weighed in a 2:1 molar ratio. Typically, when preparing compounds comprising zinc oxide, about 1 gram of zinc oxide is used. In particular embodiments, the zinc oxide molecule and molecule comprising an acidic hydrogen are placed in a glass jar with approximately 200-250 mL of alcohol solution. The glass jar may be sealed with a lid. Mixing may occur by any method known to one of skill in the art—e.g., by stirring, by stirring via a magnetic stirrer and magnetic stir bar, by sonication, by vortexing, by shaking, or by any combination of such methods.

The mixture may be sampled periodically to observe formation of the complexes. A typical reaction may take from about 7 to about 28 days.

Further, the processes of mixing zinc oxide with a molecule having an acidic hydrogen can also result in a polymeric chain of alternating zinc oxide monomers with a molecule having an acidic hydrogen. For instance, if "A" represents zinc oxide and "B" represents the molecule having an acid hydrogen, then the polymeric structure would be A/B/A/B/A/B . . . . The link between A and B would take place between zinc and the oxygen from the hydroxyl group of the acid hydrogen.

Examples of methods employed to provide specific compounds are discussed in more detail below. It is contemplated that one of skill in the art may choose to make changes to the methods employed herein to optimize production of the desired compound. Ways of altering the amounts of ingredients, conditions for mixing, mixing time, etc., are well known to those of skill in the art.

C. Compositions of the Present Invention

The compounds, as described throughout the specification, can be incorporated into compositions such as topical skin formulations or pharmaceutical formulations (e.g., oral, topical, injectable, etc.).

Additionally, the compositions can include any number of combinations of additional ingredients described throughout this specification. The concentrations of any ingredient (including the compounds disclosed herein) within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the compounds or other ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The compounds and compositions of the present invention can be incorporated into all types of cosmetically and dermalogically acceptable vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that compounds identified throughout this specification, or any combination thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

D. Products and Articles of Manufacture

The compositions of the present invention can be incorporated into cosmetic products, food-based products (e.g., fortified water, energy drinks, nutritional drinks, vitamins, supplements, solid foods), pharmaceutical products, etc. Non-limiting examples of cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

E. Delivery Systems

Some of the compounds comprising complexes of zinc oxide and a molecule comprising an acidic hydrogen have properties such that the complexes dissociate in water or when they come into contact with acids present in normal skin. For example, complexes comprising zinc oxide and lactic acid dissociate in water. Such complexes may be useful as delivery systems, and it is contemplated that zinc oxide may be used as a delivery system for any of the molecules comprising an acidic hydrogen disclosed herein. For example, the zinc oxide complexes may be useful as a delivery system for alpha-hydroxy acids, such as lactic acid, or for other acids, such as ascorbic acid, azelaic acid, or salicylic acid.

Complexes that dissociate in water may be comprised in an anhydrous product. When applied to skin, moisture from the skin would cause the zinc oxide complex to fall apart and release the molecule comprising an acidic hydrogen, such as lactic acid. Because zinc oxide has skin-calming properties, the presence of zinc oxide in the delivery system would provide some calming action. Such calming action would be particularly useful when delivering compounds that may irritate the skin, such as acidic compounds. For example, hydroxy acids have found frequent use in cosmetic applications because of, for example, their anti-aging and exfoliating effects, but such acids may be irritating to the skin. Thus, a delivery system comprising zinc oxide complexed with such acidic compounds would be useful to help alleviate skin irritation caused by the acidic compound.

It is noted that azelaic acid and salicylic acid have anti-acne properties. Thus, in particular embodiments, zinc oxide complexes are used to deliver azelaic acid or salicylic acid. Thus, it is contemplated that zinc oxide/azelaic acid complexes and zinc oxide/salicylic acid complexes will be useful in compositions for treatment of acne.

Moreover, it is noted that salicylic acid also has exfoliating properties. Thus, in particular aspects, zinc oxide/salicylic acid complexes will be useful in compositions for exfoliating skin. In certain embodiments, zinc oxide/glyceryl salicylate complexes are provided in compositions and methods of the present invention. Such zinc oxide/glyceryl salicylate complexes may also be useful in compositions for exfoliating skin.

Zinc itself has numerous health benefits and is often included in dietary and mineral supplements. Thus, it is contemplated that the compounds disclosed herein may serve as delivery systems for zinc or zinc oxide.

F. Additional Ingredients

In addition to the compounds and other ingredients disclosed throughout this specification, compositions of the present invention can include additional ingredients such as cosmetic ingredients and pharmaceutically active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents/Sunscreen Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (and octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, dibenzoylmethane derivatives (e.g., avobenzone), octocrylene, etc. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinali s extract, apricot (*Prunus armeniaca*) kernel oil, arginine, arginine aspartate, arnica montana extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota* sativa) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica* limonum) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, poly silicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

j. Skin Lightening Agents

Non-limiting examples of skin lightening agents that can be used in the context of the present invention include dipotassium glycyrrhizate, ascorbyl glucoside, niacinamide, hydroquinone, or combination thereof 2. Pharmaceutical Ingredients Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

In general, pharmaceutical compositions of the present invention should be essentially free of pyrogens, as well as other impurities that could be harmful to humans or animals. In addition, one will generally desire to employ appropriate salts and buffers. Pharmaceutical compositions of the present invention comprise an effective amount of the desired compound in a pharmaceutically acceptable carrier. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Supplementary active ingredients also can be incorporated into the compositions.

Administration of these compositions according to the present invention will be via any common route so long as the target tissue is available via that route. This includes administration by topical means and also includes systemic or parenteral methods including intravenous injection, intraspinal injection, or intracerebral, intradermal, subcutaneous, intramuscular, or intraperitoneal methods. Depending on the nature of the compound or composition, administration may also be via oral, nasal, buccal, rectal, or vaginal means. Such compositions would normally be administered as pharmaceutically acceptable compositions, described supra.

By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, followed by filtered sterilization. Generally, dispersions are prepared by incorporating the various sterilized active ingredients into a sterile vehicle, which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient plus any additional desired ingredient from a previously sterile-filtered solution thereof.

Compounds and compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition may be formulated as a "unit dose." For example, one unit dose could be dissolved in 1 ml of isotonic NaCl solution and either added to 1000 ml of hypodermoclysis fluid or injected at the proposed site of infusion, (see, e.g., "Remington's Pharmaceutical Sciences," $15^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

G. Kits

Kits are also contemplated as being used in certain aspects of the present invention. For instance, compounds or compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

H. Screening Methods

The methods of the present invention may be useful in testing additional molecules for their ability to chemically bind to zinc oxide. For example, a candidate molecule having beneficial properties and also having one or more hydrogens that may have acidic characteristics can be mixed with zinc oxide according to the methods disclosed herein to determine if the candidate molecule can chemically bind to zinc oxide. Compounds identified by these methods may then be further tested for desired characteristics and usefulness in compositions such as topical skin compositions and pharmaceutical compositions.

EXAMPLES

The following examples are included to demonstrate certain non-limiting aspects of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Compounds Comprising Zinc Oxide and Lactic Acid

Figure 6A:
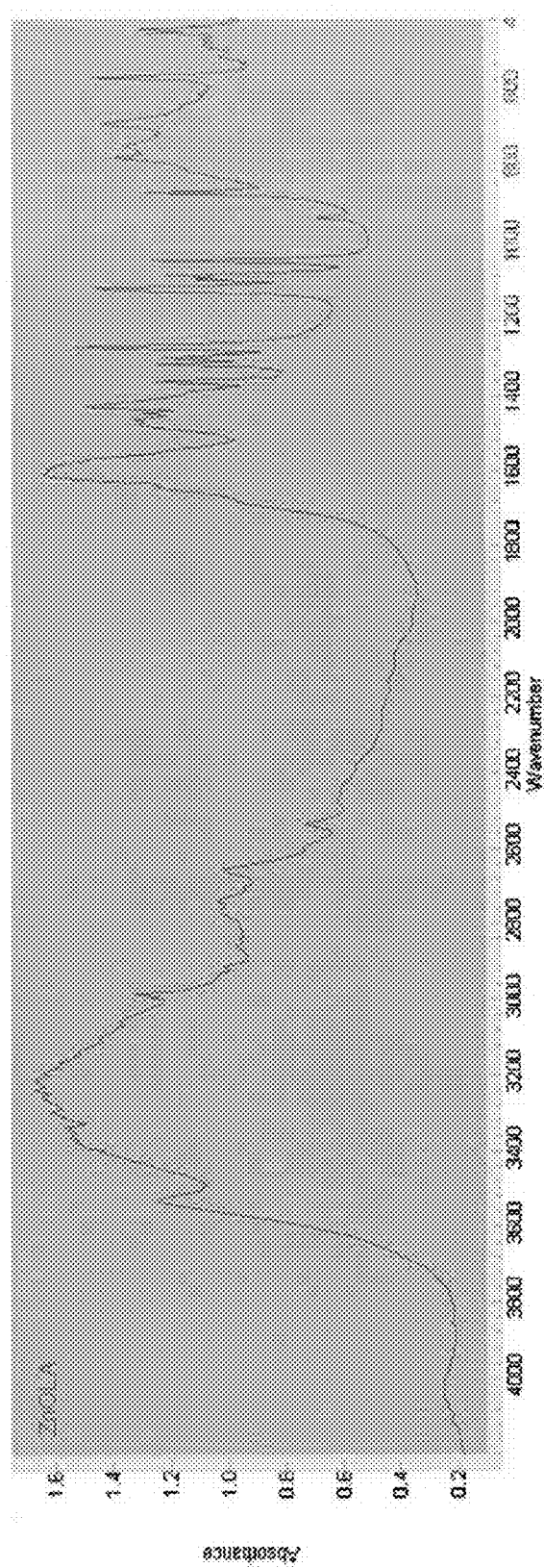
Figure 7A:
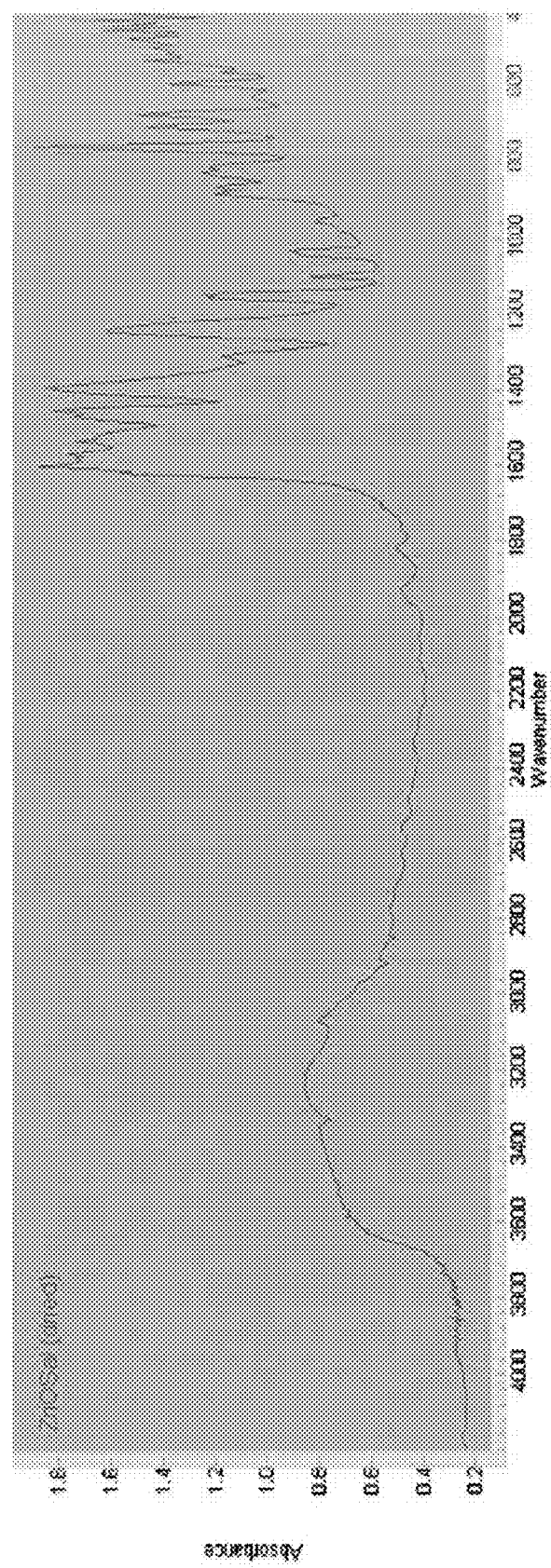
Figure 7D:
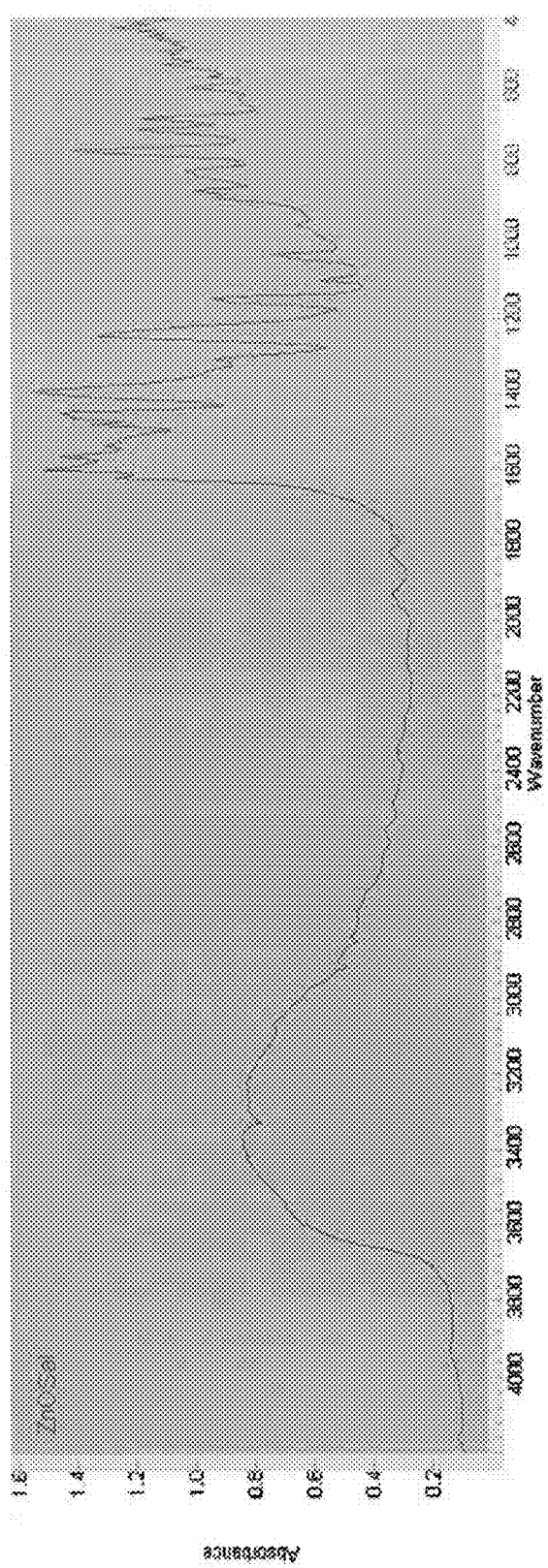

Methods of the present invention may be used to produce complexes comprising zinc oxide and alpha-hydroxy acids, such as lactic acid or glycolic acid. Here, complexes comprising zinc oxide and lactic acid were produced (see FIGS. 6A-C).

Zinc oxide and lactic acid were mixed in an ethanol solution (reagent grade ethyl alcohol denatured with methanol and isopropyl alcohol) containing approximately 10% water at room temperature with continuous stirring using a magnetic stirrer. Fine needle-like crystals were observed after approximately two weeks of mixing. The crystals were isolated by filtering. IR spectroscopy was performed and revealed the presence of zinc oxide and lactic acid in the crystals. The complexes exhibited no melting point. In water, the complexes dissociate into zinc oxide and lactic acid—i.e., the complexes are soluble in water or aqueous compositions. Analysis of the zinc oxide/lactic acid complexes revealed that the complex likely contains one molecule of zinc oxide and two molecules of lactic acid.

Because zinc oxide is a known skin-calming agent, and because the zinc oxide/lactic acid complexes readily dissociate when they contact water (such as moisture in the skin), it is contemplated that the zinc oxide/lactic acid complexes of the present invention may be useful for delivery of zinc oxide in combination with lactic acid.

The zinc oxide/lactic acid complexes were soluble in water. Specifically, approximately 0.1 g zinc oxide/lactic acid was dissolved in 10 mL of deionized water via vortexing. The solution contained no large particles. After standing overnight, the mixture settled, providing a clear liquid fraction at the top. The mixture had a pH of approximately 6. The zinc oxide/lactic acid complexes were also soluble in sodium lactate. Specifically, approximately 0.1 g zinc oxide was mixed in 10 mL sodium lactate solution (containing approximately 0.88 g sodium lactate in 10 mL deionized water). The mixture was vortexed to dissolve the particles such that no large visible particles remained. Overnight, the mixture settled, providing a clear liquid fraction at the top. The mixture had a pH of approximately 6.

To further test solubility of the zinc oxide/lactic acid complexes in a solution comprising lactic acid and water, increasing amounts of lactic acid were added to 0.725 g zinc oxide/lactic acid complexes. Specifically, the following amounts of 88% lactic acid were added to the zinc oxide/lactic acid complexes in 10 mL deionized water: 0.0273 g, 0.0262 g, 0.0345 g, 0.0575 g, 0.0757 g, 0.1166 g, 0.1562 g, 0.1389 g, 0.1486 g, and 0.2810 g. Approximately 0.3 g zinc oxide/lactic acid complexes were also mixed with 0.0670 g or 0.2517 g 88% lactic acid. All combinations produced a milky mixture that settles upon standing.

Zinc oxide/lactic acid complexes could also be formed using approximately 6.02 g 88% lactic acid mixed with approximately 4.72 g zinc oxide in 40 mL deionized water and 160 mL reagent-grade ethanol.

The zinc oxide/lactic acid complexes were used to make a hydrophobic cream composition comprising: 7.6% dimethicone (e.g., 5 g in 65.5 g total), 15.3% cetyl dimethicone (e.g., 10 g in 65.5 g total), 0.6% glyceryl tribenate (e.g., 0.4 g in 65.5 g total), 2.6% paraffin (e.g., 1.2 g in 65.5 g total), 26.6% cyclomethicone tetra (e.g., 17.4 g in 65.5 g total), 16.8% methyl methacrylate (e.g., 11 g in 65.5 g total), 22.9% trihydroxystearin cyclomethicone (e.g., 15 g in 65.5 g total), 7.6% zinc oxide/lactic acid complexes (e.g., 5 g in 65.5 g total). The composition has positive tactile attributes when placed topically on skin. For example, the composition applies smoothly onto the skin and does not have a greasy feel. Also, the composition leaves no white powder film, and does not sting the skin.

Example 2

Compounds Comprising Zinc Oxide and Glycolic Acid

Methods of the present invention were used to produce complexes comprising zinc oxide and glycolic acid. 70% DuPont Technical Grade Glycolic Acid was used. Approximately 0.1 grams of zinc oxide was mixed with 0.27 grams glycolic acid. Mixing was in 200-250 mL reagent grade ethyl alcohol (denatured with methanol and isopropyl alcohol). Mixing was at room temperature with continuous stirring using a magnetic stirrer. After about 11 days, the zinc oxide/glycolic acid complexes could be visualized as crystals in the alcohol solution.

Example 3

Compounds Comprising Zinc Oxide and Hydroxyproline

Figure 5:
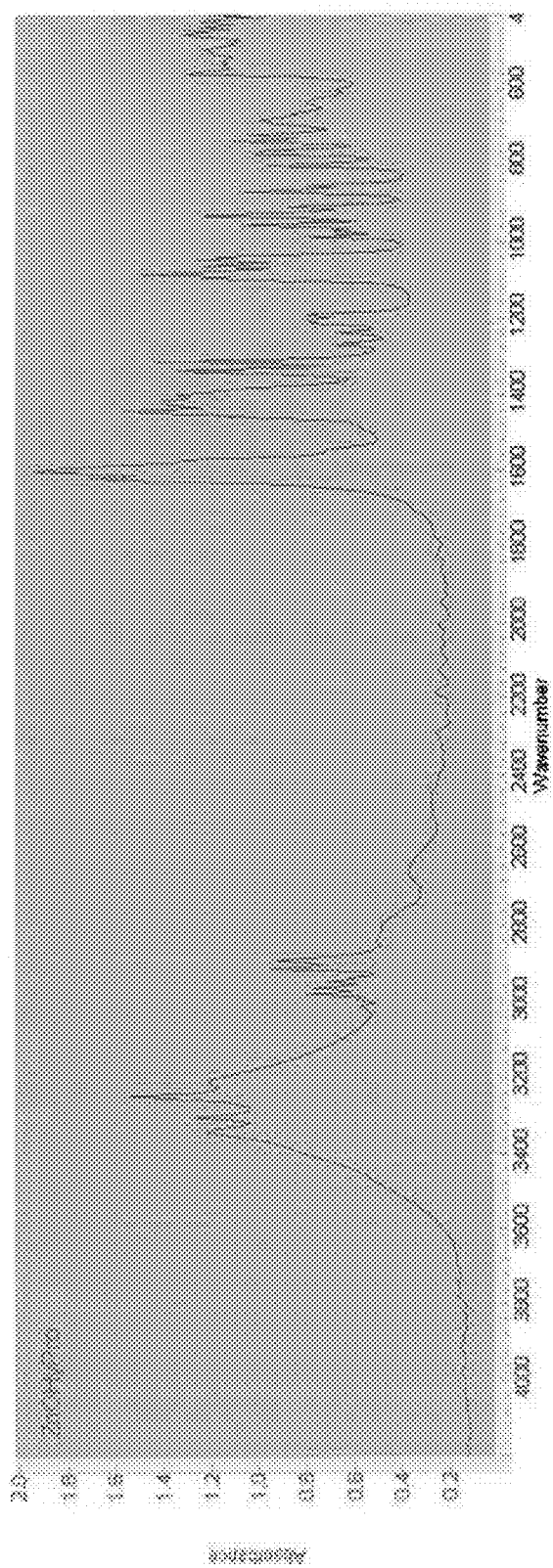
FIG. 5: Infrared data concerning a zinc oxide/hydroxyproline compound.

The methods of the present invention may be used to produce complexes comprising zinc oxide and an amino acid, such as hydroxyproline. Here, complexes comprising zinc oxide and hydroxyproline were produced (see FIG. 5). Approximately 1 g zinc oxide was mixed with approximately 1.6 g hydroxyproline in approximately 200 mL anhydrous alcohol. Mixing was by magnetic stirrer in a 16 oz. glass jar at ambient temperature.

The complexes formed within 7 days and were isolated by filtering (with a Buchner funnel) after about 14 days with a yield of approximately 91.2%. The complexes had no observable melting point, and IR spectroscopy revealed that both zinc oxide and hydroxyproline were present in the complexes.

Example 4

Compounds Comprising Zinc Oxide and Azaleic Acid

Figure 2A:
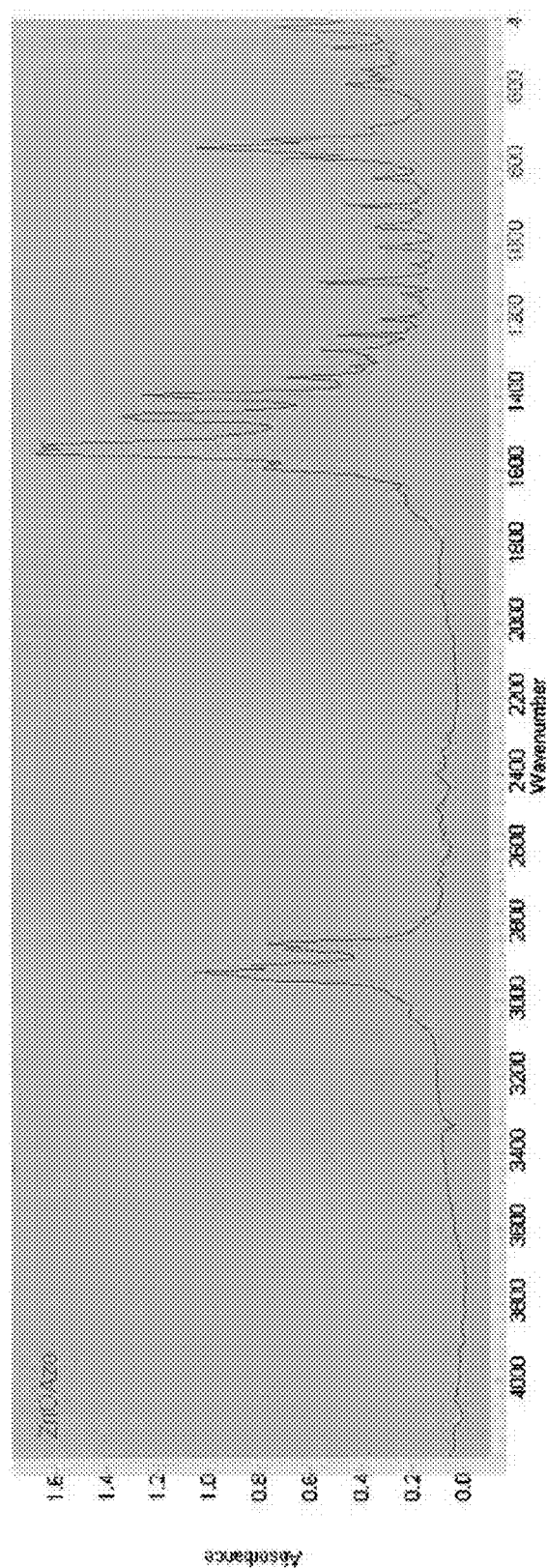

The methods of the present invention may be used to produce complexes comprising zinc oxide and a di-acid, such as azaleic acid. Complexes comprising zinc oxide and azaleic acid were produced (see FIGS. 2A-C), and had no observable melting point. IR spectroscopy confirmed that the complexes contain both zinc oxide and azelaic acid. Mixing was in 200-250 mL reagent grade ethyl alcohol (denatured with methanol and isopropyl alcohol) at room temperature with continuous stirring using a magnetic stirrer.

Azelaic acid has known anti-acne properties. Thus, it is contemplated that zinc oxide/azelaic acid complexes may be useful in treating acne and as an ingredient in compositions for treating acne.

Example 5

Compounds Comprising Zinc Oxide and Oleic Acid

Figure 4A:
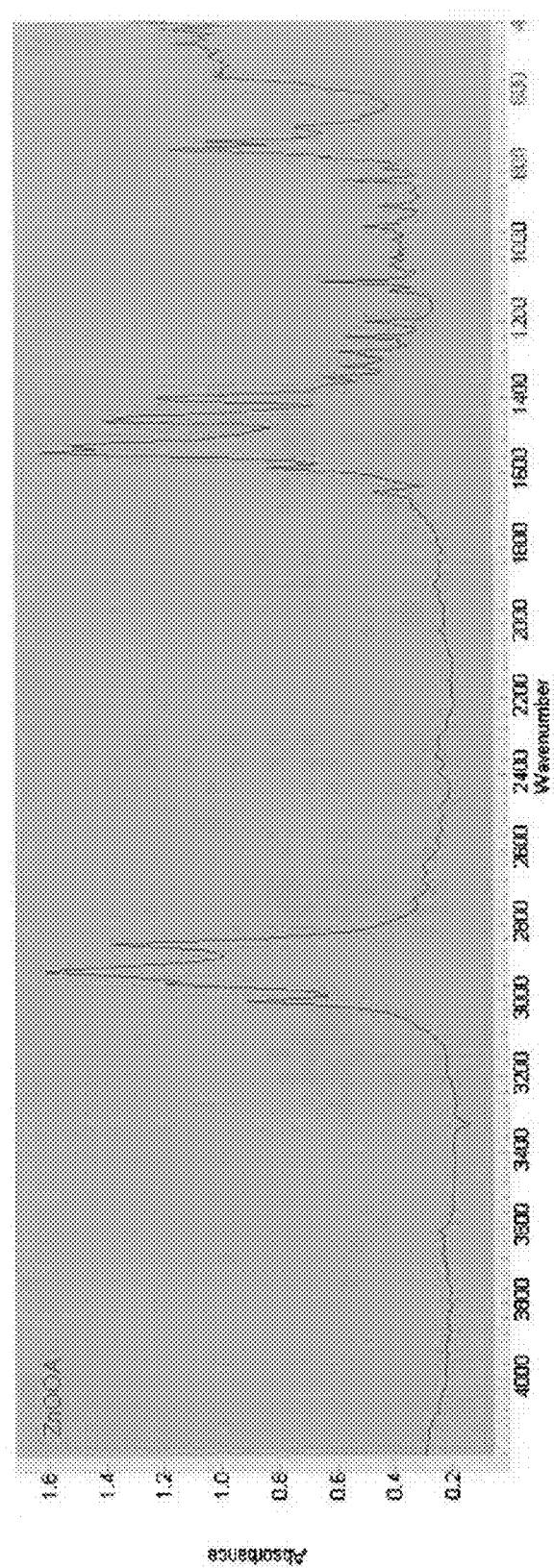

The methods of the present invention may be used to produce complexes comprising zinc oxide and a carboxylic acid, such as oleic acid. Here, complexes comprising zinc oxide and oleic acid were produced (see FIGS. 4A-C). Approximately 1 g zinc oxide was mixed with about 3.47 g oleic acid in 200 mL anhydrous reagent-grade ethanol (denatured with methanol and isopropyl alcohol). The molecules were mixed for approximately three weeks at ambient temperature using a magnetic stirrer.

The complexes comprising zinc oxide and oleic acid were solid particles and were isolated by filtering (#41 Whatman filter paper) with a yield of approximately 75.4%. The complexes had no observed melting point, and IR spectroscopy confirmed the presence of both zinc oxide and oleic acid in the complexes. The zinc oxide/oleic acid complexes did not dissociate easily in water.

Because of the beneficial textural properties of compositions comprising zinc oxide/oleic acid complexes, such complexes may be particularly useful in foundations, pressed powders (such as for skin, eyes, cheeks, etc.), sunscreen, loose powder products, or lipsticks, lip glosses, or lip balms.

Example 6

Compounds Comprising Zinc Oxide and Salicylic Acid

The methods of the present invention may be used to produce complexes comprising zinc oxide and an aromatic acid, such as salicylic acid. Here, complexes comprising zinc oxide and salicylic acid were produced (see FIGS. 7A-F). Approximately 1 g zinc oxide was mixed with about 1.7 g salicylic acid in 200 mL anhydrous reagent grade ethyl alcohol. The molecules were mixed in a 16 oz. glass jar using a magnetic stirrer at ambient temperature.

Complexes were observed after approximately 14 to 19 days. After 19 days, the complexes were isolated by filtering (via a Buchner funnel) with an approximate yield of 79.1%. The complexes comprising zinc oxide and salicylic acid had no observed melting point, and IR spectroscopy confirmed that the complexes contain zinc oxide and salicylic acid. The complexes do not dissociate easily in water.

Complexes could also be formed by combination of approximately 0.86 g salicylic acid, 0.25 g zinc oxide, 10 mL deionized water, and 20 mL acetone. Using the same methods, complexes could also be formed by mixing approximately 0.26 g zinc nitrate and approximately 0.23 g salicylic acid.

Example 7

Compounds Comprising Zinc Oxide and Ascorbic Acid

The methods of the present invention were used to produce complexes comprising zinc oxide and ascorbic acid. Zinc oxide molecules and ascorbic acid molecules were mixed in a 1:1 molar ratio in the presence of an alcohol (mixture of methanol and isoppropanol) that had been purged with nitrogen gas in order to remove oxygen. A nitrogen blanket was placed over the mixture, and the container was sealed. The container and seal were covered with black electrical tape to exclude light. An additional opaque external container was placed around the container housing the mixture in order to further prevent light from reaching the mixture. Mixing was by continuous stirring on a magnetic stirrer at room temperature.

Mixing was for approximately two weeks. The zinc oxide/ascorbic acid complexes prepared by the disclosed methods may be isolated by evaporating the alcohol in the solution, such as by use of a roto-evaporator or by spray drying techniques. The produced zinc oxide/ascorbic acid complex was in crystalline form and was found to be soluble in alcohol.

Such zinc oxide/ascorbic acid complexes may be particularly useful as a delivery system for ascorbic acid. Such complexes may also be useful to stabilize ascorbic acid in various compositions.

Example 8

Compounds Comprising Zinc Oxide and Avobenzone

Figure 3A:
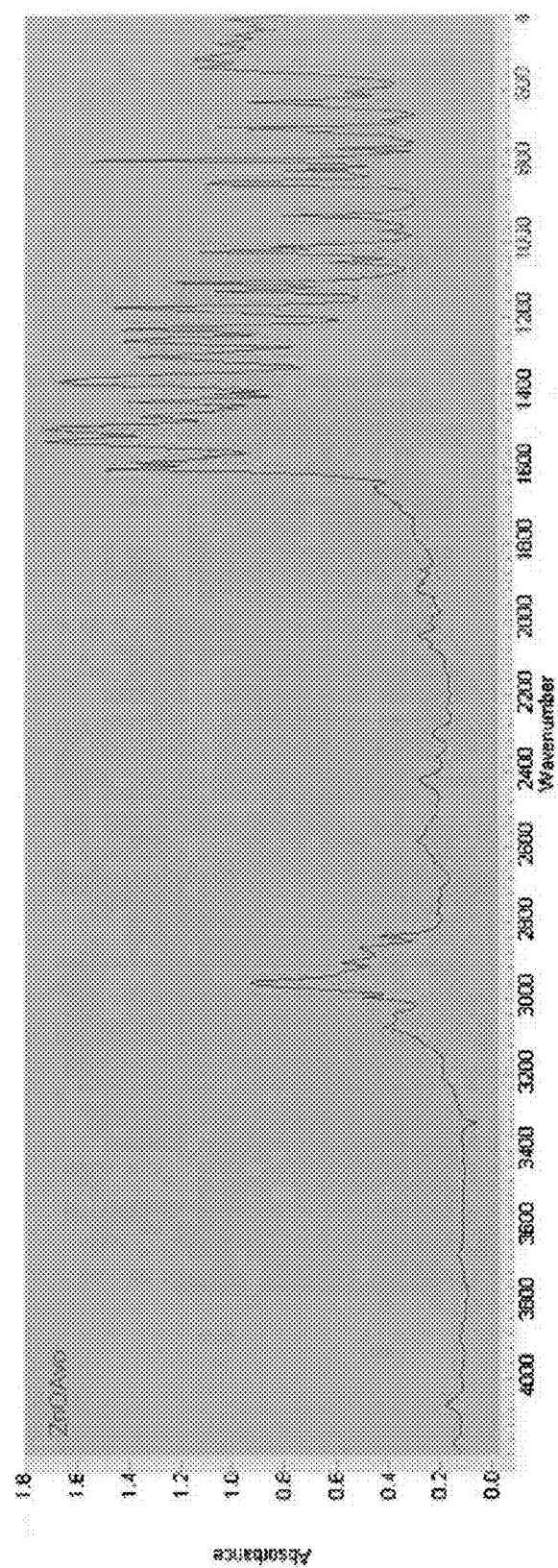

The methods of the present invention were used to produce complexes comprising zinc oxide and avobenzone (Parsol 1789 was the source for avobenzone) (see FIGS. 3A-C). Approximately 1 g zinc oxide was mixed with about 3.8 g Parsol 1789 in 250 mL anhydrous alcohol (mixture of methanol and isoppropanol). Mixing occurred in a sealed glass jar on a magnetic stirrer at ambient temperature. Complexes were visible within nine days of mixing. The complexes were isolated by filtering (via a Buchner funnel) after about 21 days of mixing, and the yield was approximately 92.5%. The zinc oxide/avobenzone complexes formed had no observable melting point, and IR spectroscopy confirmed that the complexes contained zinc oxide and avobenzone.

The zinc oxide/avobenzone compounds of the present invention are particularly useful in sunscreen compositions because such compounds combine the physical sunscreen properties of zinc oxide with the chemical sunscreen properties of avobenzone. The presence of avobenzone in complexes with zinc oxide may stabilize the avobenzone in sunscreen compositions.

Example 9

Compounds Comprising Zinc Oxide and Kojic Acid

Compounds comprising zinc oxide and Kojic Acid were produced according to methods of the present invention. The complexes were prepared in reagent-grade alcohol containing approximately 10% deionized water. Zinc oxide and Kojic Acid were combined in a 1:1 molar ration, and mixing was in 200-250 mL anhydrous reagent grade ethyl alcohol (denatured with methanol and isopropyl alcohol). Mixing was at room temperature with continuous stirring using a magnetic stirrer. The complexes could be visualized as clumps of crystals, which started to appear after just one day of mixing.

Example 10

Compounds Comprising Zinc Oxide and Citric Acid

Compounds comprising zinc oxide and citric acid were produced according to methods of the present invention. Zinc oxide and anhydrous citric acid were mixed in a solution containing 90% reagent-grade ethanol and 10% deionized water. The molecules were mixed in a 1:1 molar ratio (e.g., approximately 0.24 grams citric acid mixed with about 0.1 grams zinc oxide in 20 mL 90% ethanol solution). Zinc oxide and citric acid molecules were also mixed in a 2:1 molar ratio (e.g., approximately 0.12 grams citric acid mixed with about 0.1 grams zinc oxide in 20 mL 90% ethanol solution). The molecules were mixed by sonication for approximately four minutes. The molecules were then mixed by magnetic stirrer at room temperature, and complex formation was observed.

Example 11

Compounds Comprising Zinc Oxide and Malic Acid

Compounds comprising D-malic acid and zinc oxide were produced by methods of the invention. Approximately 0.076 g zinc oxide was mixed with about 0.136 g D-malic acid in 200-250 mL anhydrous reagent grade ethyl alcohol (denatured with methanol and isopropyl alcohol). The solution was sonicated for approximately 30 minutes. Five drops of citric acid was added to half of the solution, and the solutions were mixed for approximately two days at room temperature with continuous stirring using a magnetic stirrer. Both solutions exhibited crystals representing zinc oxide/malic acid complexes.

The same methods were employed to form zinc oxide/malic acid complexes using L-malic acid or a combination of D-malic acid and L-malic acid. To make complexes comprising zinc oxide and L-malic acid, approximately 0.766 g zinc oxide was added to about 0.137 g L-malic acid in 200-250 mL anhydrous reagent grade ethyl alcohol (denatured with methanol and isopropyl alcohol). Mixing was at room temperature with continuous stirring using a magnetic stirrer. To make complexes comprising zinc oxide and L-malic acid or D-malic acid, approximately 0.0.78 g zinc oxide was added to approximately 0.056 g D-malic acid and 0.0704 g L-malic acid in 200-250 mL anhydrous reagent grade ethyl alcohol (denatured with methanol and isopropyl alcohol). Mixing was at room temperature with continuous stirring using a magnetic stirrer.

Example 12

Additional Assays that can be Used to Test Compositions

The efficacy and usefulness of any of the compounds and compositions of the present invention can be determined by methods known to those of ordinary skill in the art. The following are non-limiting assays that can be used in the context of the present invention. It should be recognized that other testing procedures can be used, including, for example, objective and subjective procedures.

Skin Firmness and Elasticity Assay with a Hargens Ballistometer: Skin firmness and elasticity can be measured using a Hargens ballistometer, a device that evaluates the firmness and elasticity of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Dryness, Surface Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Skin Smoothness and Wrinkle Reduction Assay with Methods Disclosed in Packman et al. (1978): Skin smoothness and wrinkle reduction can also be assessed visually by using the methods disclosed in Packman and Gams (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt, which is the maximum vertical distance between the highest peak and lowest trough, and Rz, which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b2)^{1/2}$.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of vulcanizing rubber, the method comprising adding to un-vulcanized rubber a complex comprising mercaptobenzothiazole chemically bound to zinc oxide, and vulcanizing the rubber.

2. The method of claim 1, wherein the complex is in crystal form when combined with the un-vulcanized rubber.

3. The method of claim 1, wherein the mercaptobenzothiazole is covalently bound to the zinc oxide.

4. The method of claim 3, wherein the mercaptobenzothiazole is covalently bound to the zinc atom of the zinc oxide.

5. The method of claim 1, wherein the oxygen atom of the zinc oxide is covalently bound to an acidic hydrogen from the mercaptobenzothiazole.

6. A vulcanizing accelerator comprising a complex comprising mercaptobenzothiazole chemically bound to zinc oxide.

7. The vulcanizing accelerator of claim 6, wherein the complex is in crystal.

8. The vulcanizing accelerator of claim 6, wherein the mercaptobenzothiazole is covalently bound to the zinc oxide.

9. The vulcanizing accelerator of claim 8, wherein the mercaptobenzothiazole is covalently bound to the zinc atom of the zinc oxide.

10. The vulcanizing accelerator of claim 6, wherein the oxygen atom of the zinc oxide is covalently bound to an acidic hydrogen from the mercaptobenzothiazole.

* * * * *